(12) United States Patent
Shimizu et al.

(10) Patent No.: US 10,647,973 B2
(45) Date of Patent: May 12, 2020

(54) MANNANASE AND USE THEREOF

(71) Applicant: MEIJO UNIVERSITY EDUCATIONAL FOUNDATION, Nagoya-shi, Aichi (JP)

(72) Inventors: Motoyuki Shimizu, Nagoya (JP); Masashi Kato, Nagoya (JP)

(73) Assignee: MEIJO UNIVERSITY EDUCATIONAL FOUNDATION, Nagoya-shi (JP)

(*) Notice: Subject to any disclaimer, the term of this patent is extended or adjusted under 35 U.S.C. 154(b) by 0 days.

(21) Appl. No.: 15/553,535

(22) PCT Filed: Feb. 29, 2016

(86) PCT No.: PCT/JP2016/056141
§ 371 (c)(1),
(2) Date: Aug. 24, 2017

(87) PCT Pub. No.: WO2016/137008
PCT Pub. Date: Sep. 1, 2016

(65) Prior Publication Data
US 2018/0016565 A1    Jan. 18, 2018

(30) Foreign Application Priority Data
Feb. 27, 2015    (JP) .................. 2015-039405

(51) Int. Cl.
*C12N 9/26* (2006.01)
*C12N 15/00* (2006.01)
*C12N 1/20* (2006.01)
*C07H 21/04* (2006.01)
*C12N 9/24* (2006.01)
*C13K 13/00* (2006.01)
(Continued)

(52) U.S. Cl.
CPC ............. *C12N 9/2494* (2013.01); *C12N 9/24* (2013.01); *C12N 15/63* (2013.01); *C12N 15/70* (2013.01); *C12P 19/02* (2013.01); *C12P 19/14* (2013.01); *C13K 13/00* (2013.01)

(58) Field of Classification Search
None
See application file for complete search history.

(56) References Cited

U.S. PATENT DOCUMENTS

| | | |
|---|---|---|
| 2004/0082053 A1 | 4/2004 | Machida et al. |
| 2005/0142650 A1 | 6/2005 | Yuuki et al. |
| 2006/0234320 A1 | 10/2006 | Machida et al. |

FOREIGN PATENT DOCUMENTS

| | | |
|---|---|---|
| JP | 2001-145484 A | 5/2001 |
| JP | 2005-176602 A | 7/2005 |

(Continued)

OTHER PUBLICATIONS

Galagan. Q5B9S0. UniProtKB. 2014.*
(Continued)

*Primary Examiner* — Yong D Pak
(74) *Attorney, Agent, or Firm* — Oliff PLC

(57) ABSTRACT

A novel mannanase. A polypeptide having a specific amino acid sequence such as the amino acid represented by SEQ ID NO:2 exhibits a mannanase activity. Although this mannanase does not have homology with known mannanase at the amino acid level, the polypeptide has a mannanase activity as well as heat resistance.

10 Claims, 17 Drawing Sheets
Specification includes a Sequence Listing.

| No | Annotation name |
|---|---|
| 1 | Putative chitinase (GH18) |
| 2 | Endo-1,4-β-mannanase (GH5) |
| 3 | Putative endo-1,4-β-mannanase (GH5) |
| 4 | Putative endo-1,4-β-mannanase (GH5) |
| 5 | Putative trypsin-like protease |
| 6 | Putative dipeptidyl-peptidase |
| 7 | Hypothetical protein |

(51) Int. Cl.
  *C12N 15/70* (2006.01)
  *C12N 15/63* (2006.01)
  *C12P 19/02* (2006.01)
  *C12P 19/14* (2006.01)

(56) References Cited

FOREIGN PATENT DOCUMENTS

| JP | 2009-060805 A | | 3/2009 |
|---|---|---|---|
| JP | 2011-083275 A | | 4/2011 |
| JP | 2013-516960 A | | 5/2013 |
| WO | 2011/085747 A1 | | 7/2011 |
| WO | WO 2016/056662 | * | 4/2016 |

OTHER PUBLICATIONS

Rosano. Recombinant protein expression in *Escherichia coli*: advances and challenges. Front Microbiol. 2014; 5: 172. Published online Apr. 17, 2014.*
Galagan. Sequencing of Aspergillus nidulans and comparative analysis with A. fumigatus and A. oryzae. Nature 438:1105-1115(2005).*
CBF84169. 2009.*
Machine Translation of WO 2016/056662. retrieved on Feb. 28, 2018 via https://www4.j-platpat.inpit.go.jp/cgi-bin/tran_web_cgi_ejje?u=http://www4.j-platpat.inpit.go.jp/eng/translation/201902280 645024975682143254567139816C83F759B68711849ED3A14C0E FE4E[Feb. 27, 2019 4:45:50 PM].*
Studer. Residue mutations and their impact on protein structure and function: detecting beneficial and pathogenic changes. Biochem. J. (2013) 449, 581-594.*
Sakai, K., et al, "Biochemical characterization of thermostable β-1,4-mannanase belonging to the glycoside hydrolase family 134 from Aspergillus oryzae", Appl Microbiol Biotechnol, vol. 101, p. 3237-3245, 2017.
Jin, Y., et al. "Aβ-Mannanase with a Lysozyme-like Fold and a Novel Molecular Catalytic Mechanism", ACS central science, p. 27-34, 2016.
Shimizu, M., et al., "Novel β-1,4-Mannanase Belonging to a New Glycoside Hydrolase Family in Aspergillus nidulans", The Journal of Biological Chemistry, vol. 290, No. 46, p. 27914-27927, 2015.
Database EMBL/GenBank, "Aspergillus nidulans FGSC A4 chromosome VI ANcontig1.47, whole genome shotgun sequence", No. EAA63112.1, 2016.
Database EMBL/GenBank, "Aspergillus nidulans FGSC A4 chromosome I ANcontig1.115, whole genome shotgun sequence", No. EAA57706.1, 2016.
Misawa, K., et al., "A method to identify cDNAs based on localization of green fluorescent protein fusion products", Proc. Natl. Acad. Sci., vol. 97, No. 7, p. 3062-3066, 2000.
Larsson, M., et al. "High-throughput protein expression of cDNA products as a tool in functional genomics", Journal of Biotechnology, vol. 80, p. 143-157, 2000.
Sawasaki, T., et al., "A cell-free protein synthesis system for high-throughput proteomics", Proc. Natl. Acad. Sci., vol. 99, p. 14652-14657, 2002.
Saaya Ishihara, et al., "Aspergillus nidulans ga Saibogai ni Bunpitsu suru β-Mannan Bunkai ni Kan'yo suru Shinki Tanpakushitsu no Kino Kaiseki", Japan Society for Bioscience, Biotechnology, and Agrochemistry Soritsu 90 Shunen Chubu Shibu Soritsu 60 Shunen Kinen Dai 171 Kai Reikai Koen Yoshishu, vol. 11, 2014.
May 24, 2016 International Search Report issued in International Patent Application No. PCT/JP2016/056141.
May 24, 2016 Written Opinion of the International Searching Authority issued in International Patent Application No. PCT/JP2016/056141.
Dec. 3, 2019 Office Action issued in Japanese Patent Application No. 2017-502541.

* cited by examiner

Std;
Mannobiose(M2),Mannnotoriose(M3),
Mannotetraose(M4),
Mannopentaose(M5),
Mannnohexose(M6)

1; rMan5C
2; HP

| Enzymes | Substrate | $K_m$ (mg/ml) | $k_{cat}$ ($s^{-1}$) | $k_{cat}/K_m$ ($ml\ s^{-1}\ mg^{-1}$) |
|---|---|---|---|---|
| HP | Glucomannan | 1.2 ± 0.1 | 390 ± 30 | 330 |
| | Galactomannan | 4.7 ± 0.2 | 240 ± 20 | 51 |
| Man5C | Glucomannan | 0.81 ± 0.1 | 540 ± 40 | 620 |
| | Galactomannan | 2.7 ± 0.2 | 200 ± 20 | 74 |

Optimal temperature of rHP

| Organism | Name | Identities with SEQ ID:2 |
|---|---|---|
| A. nidulans | SEQ ID:2 (2710) | 100% |
| | SEQ ID:4 (6833) | 70% |
| | SEQ ID:6 (6951) | 54% |
| A. oryzae | SEQ ID:8 (0445) | 71% |
| Streptomyces sp | SEQ ID:10 134 | 61% |

Fig. 16

|  | Km (mg/ml) | kcat (s⁻¹) | kcat/Km (ml s⁻¹ mg⁻¹) |
|---|---|---|---|
| Man134A | 9.8 | 870 | 100 |
| E61A | — | — | — |
| E63A | — | — | — |
| D73A | 2.7 | 34 | 13 |
| D78A | 5.3 | 420 | 67 |
| E106A | 2.3 | 100 | 35 |
| W166A | 4.5 | 640 | 140 |
| N116A | 4.9 | 260 | 43 |

Fig.17

MANNANASE AND USE THEREOF

TECHNICAL FIELD

The present specification relates to mannanase and use thereof.

BACKGROUND ART

Mannan is a collective term for polysaccharides mainly containing mannose and is widely distributed throughout nature. Mannan includes glucomannan having a main chain formed with glucose and mannose contained in cell walls of softwood and konjac and galactomannan having a main chain formed with mannose and galactose contained in coffee beans and fruits. Because mannan exists in the form of gel, mannan is used as a thickening agent or a stabilizing agent for food products. Moreover, as mannan prevents extraction of coffee due to properties thereof, the extraction efficiency of coffee is increased by addition of mannanase (mannan decomposing enzyme).

Fungi and mushrooms secrete mannanase extracellularly to decompose mannan, thereafter intracellularly introducing and utilizing the decomposed low molecules. Various mannanases have been found so far and are utilized for manufacture of food products and industrial applications.

Mannanase generally has an optimal pH around acidic or neutral pH and an optimal temperature of around 40° C. to 70° C. Mannanases having improved heat resistance, by, for example, modification have also been reported (Patent Literature 1).

SUMMARY OF INVENTION

Many plants contain mannans which present obstacles for industrial utilization thereof due to high viscosity. Thus, if efficient mannan decomposition is available, technology transfer is expected in manufacture of food products containing mannan and biomass utilization. However, the only available technique for improving utilization of mannan is decomposition into low molecules.

Mannanase is utilized for, in addition to food applications typically including coffee extraction, industrial applications such as pulp bleaching and inclusion into detergents. When utilized in such wide areas, decomposition of mannan is carried out under various conditions. Thus, mannanase having a unique property different from existing mannanases can be effective in efficient decomposition of mannan.

Thus, an object of the present specification is to provide a novel mannanase.

Solution to Technical Problem

The inventors of the present invention found, while studying a reduction of viscosity of mannan, a novel protein derived from *Aspergillus nidulans* (*A. nidulans*), which specifically hydrolyzes mannan. By examining the protein, the inventors found that the protein has mannanase activity although the protein has no homology with existing mannanases at an amino acid level.

The inventors of the present invention also found novel mannanases derived from *Aspergillus oryzae* (*A. oryzae*) and *Streptomyces*. sp.

The present specification is based on the findings above and provides the following.

(1) A mannanase having a polypeptide selected from the group consisting of (a) to (f) below:

(a) a polypeptide having an amino acid sequence of SEQ ID NO: 2;

(b) a polypeptide having an amino acid sequence which has 70% or more identity with the amino acid sequence of SEQ ID NO: 2;

(c) a polypeptide having an amino acid sequence derived from the amino acid sequence of SEQ ID NO: 2 by substitution, deletion and/or insertion of one or a plurality of amino acids;

(d) a polypeptide encoded by DNA which, under stringent conditions, hybridizes to DNA comprising a base sequence encoding the amino acid sequence of SEQ ID NO: 2 or a complementary base sequence thereof;

(e) a polypeptide encoded by a base sequence which has 70% or more identity with a base sequence of SEQ ID NO: 1; and (f) a polypeptide encoded by DNA which, under stringent conditions, hybridizes to DNA comprising a base sequence of SEQ ID NO: 1 or a complementary base sequence thereof.

(2) The mannanase according to (1), which is derived from *Aspergillus nidulans*.

(3) An expression vector containing a polynucleotide encoding the mannanase according to (1) or (2) and one or two or more elements for expression of the polynucleotide.

(4) A transformed cell containing the expression vector according to (3).

(5) The transformed cell according to (4), which is *Escherichia coli* (*E. coli*).

(6) A method for producing the mannanase according to (1) or (2), including:

a step of culturing the transformed cell according to (4) or (5); and a step of recovering a polypeptide from the culture.

(7) A method for producing the mannanase according to (1) or (2), including:

a step of culturing the transformed cell according to (4) or (5) under a condition allowing production of the mannanase; and a step of recovering the mannanase from the culture.

(8) A method for producing a decomposed product from mannan, including a step of decomposing a mannan-containing material using the mannanase according to (1) or (2).

(9) The method according to (8), wherein the mannan-containing material is decomposed at a temperature of 70° C. or higher.

(10) A mannanase having a polypeptide selected from the group consisting of (a) to (f) below:

(a) a polypeptide having an amino acid sequence of SEQ ID NO: 8;

(b) a polypeptide having an amino acid sequence which has 70% or more identity with the amino acid sequence of SEQ ID NO: 8;

(c) a polypeptide having an amino acid sequence derived from the amino acid sequence of SEQ ID NO: 8 by substitution, deletion and/or insertion of one or a plurality of amino acids;

(d) a polypeptide encoded by DNA which, under stringent conditions, hybridizes to DNA comprising a base sequence encoding the amino acid sequence of SEQ ID NO: 8 or a complementary base sequence thereof;

(e) a polypeptide encoded by a base sequence which has 70% or more identity with the base sequence of SEQ ID NO: 7; and (f) a polypeptide encoded by DNA which, under stringent conditions, hybridizes to DNA comprising a base sequence of SEQ ID NO: 7 or a complementary base sequence thereof.

(11) The mannanase according to (10), which is derived from *Aspergillus oryzae*.

(12) An expression vector containing a polynucleotide encoding the mannanase according to (10) or (11) and one or two or more elements for expression of the polynucleotide.

(13) A transformed cell containing the expression vector according to (12).

(14) The transformed cell according to (13), which is *Escherichia coli*.

(15) A method for producing the mannanase according to (10) or (11), including:
  a step of culturing the transformed cell according to (13) or (14); and
  a step of recovering a polypeptide from the culture.

(16) A method for producing the mannanase according to (10) or (11), including:
  a step of culturing the transformed cell according to (13) or (14) under a condition allowing production of the mannanase; and
  a step of recovering the mannanase from the culture.

(17) A method for producing a decomposed product from mannan, including a step of decomposing a mannan-containing material using the mannanase according to (10) or (11).

(18) The method according to (17), wherein the mannan-containing material is decomposed at a temperature of 70° C. or higher.

(19) A mannanase, which is a polypeptide having an amino acid sequence
  including, when aligned with an amino acid sequence of SEQ ID NO: 2, a first motif consisting of WFAGHRNGXSG (wherein X represents any amino acid) corresponding to positions 138 to 148 in the amino acid sequence, a second motif consisting of DLAI/VAMLE corresponding to positions 54 to 61 in the amino acid sequence, a third motif consisting of NFGI/LFKQNW corresponding to positions 81 to 89 in the amino acid sequence and DTRFWVX$_1$VX$_2$AI (wherein X$_1$ and X$_2$ respectively and independently represent any amino acid) corresponding to positions 181 to 191 in the amino acid sequence; and
  having 54% or more identity with the amino acid sequence of SEQ ID NO: 2.

(20) The mannanase according to (19), wherein the polypeptide has the amino acid sequence further containing, when aligned with the amino acid sequence of SEQ ID NO: 2, amino acids corresponding to amino acids of positions 27 (R), 31 (G), 34 (T), 37 to 39 (GLG), 41 and 42 (RK), 48 to 50 (AGG), 65 (M), 69 (Y), 71 to 73 (YGD), 75 (K), 78 (D), 92 and 93 (LR), 117 (S), 122 and 123 (DV), 133 and 134 (YG), 152 (P), 154 (T), 156 and 157 (DI), 160 (Y), 163 and 164 (AV), 166 and 167 (WI) and 170 (Q) in the amino acid sequence of SEQ ID NO: 2.

(21) The mannanase according to (19), which is a polypeptide selected from:
  a polypeptide having an amino acid sequence which has 90% or more identity with the amino acid sequence of SEQ ID NO: 2;
  a polypeptide having an amino acid sequence which has 90% or more identity with an amino acid sequence of SEQ ID NO: 4;
  a polypeptide having an amino acid sequence which has 90% or more identity with an amino acid sequence of SEQ ID NO: 6;
  a polypeptide having an amino acid sequence which has 90% or more identity with an amino acid sequence of SEQ ID NO: 8; and
  a polypeptide having an amino acid sequence which has 90% or more identity with an amino acid sequence of SEQ ID NO: 10.

(22) The mannanase according to (20), which is a polypeptide selected from:
  a polypeptide having an amino acid sequence which has 95% or more identity with the amino acid sequence of SEQ ID NO: 2;
  a polypeptide having an amino acid sequence which has 95% or more identity with an amino acid sequence of SEQ ID NO: 4;
  a polypeptide having an amino acid sequence which has 95% or more identity with an amino acid sequence of SEQ ID NO: 6;
  a polypeptide having an amino acid sequence which has 95% or more identity with an amino acid sequence of SEQ ID NO: 8; and
  a polypeptide having an amino acid sequence which has 95% or more identity with an amino acid sequence of SEQ ID NO: 10.

The present specification provides: an expression vector containing a polynucleotide encoding the mannanase according to the above respective embodiments and one or two or more elements for expressing the polynucleotide; a transformed cell containing the expression vector; the transformed cell which is *Escherichia coli*; a method for producing the mannanase according to the respective embodiments, including a step of culturing the transformed cell and a step of recovering a polypeptide from the culture; a method for producing a decomposed product from mannan, including a step of decomposing a mannan-containing material using the mannanase according to the respective embodiments; and the like.

BRIEF DESCRIPTION OF DRAWINGS

FIG. 16 shows an alignment result of homologues and orthologues of rHP; and

FIG. 17 shows a measurement result of enzymatic parameters of alanine substitution mutants of rHP.

DESCRIPTION OF EMBODIMENTS (Mannanase)

Figure 1:
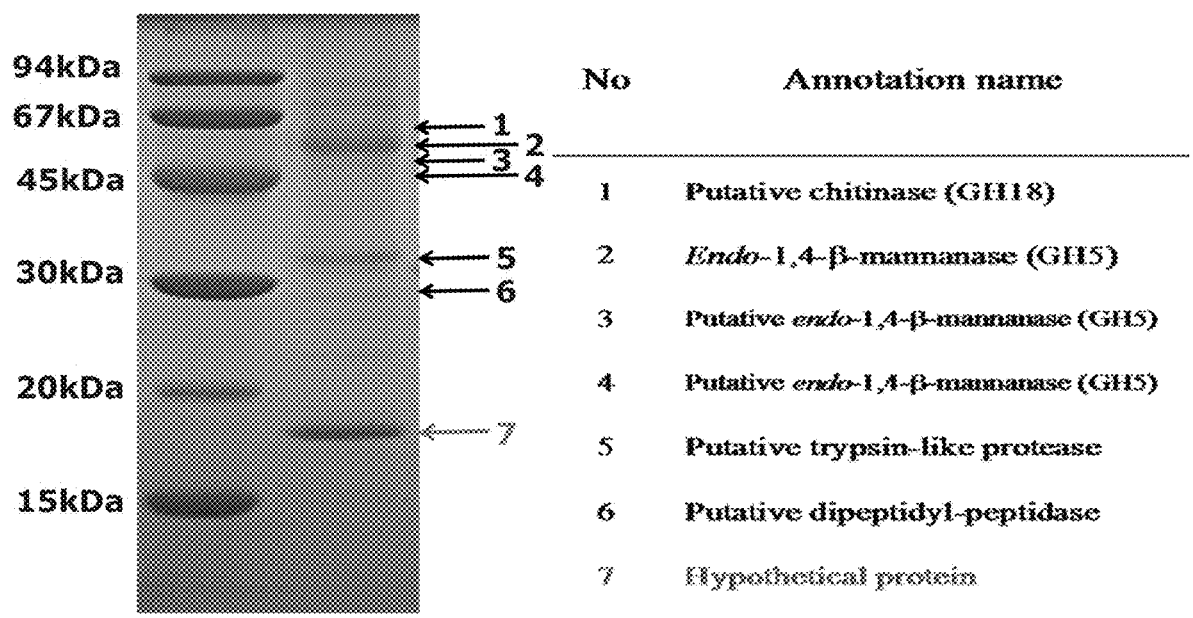
FIG. 1 shows SDS-PAGE analysis of proteins obtained from a filtered culture solution of *A. nidulans* grown in a glucomannan medium and proteins identified by MALDI-TOF/TOF-MS.

The disclosure herein relates to a novel mannanase and use thereof.

The mannanase disclosed herein has increased heat resistance compared to existing mannanases, and therefore is expected to be utilized for mannan decomposition under increased temperature conditions.

The mannanase disclosed herein is an endoenzyme hydrolyzing 1,4-β-mannoside linkages of mannan and is also referred to as β-mannanase and β-mannosidase. According to the EC classification of enzymes, the mannanase may be classified into EC3.2.1.78.

Conventional mannanases are classified into GH5, GH26 and the like according to the classification provided in the CAZy (Carbohydrate-Active enZYmes) website (www.cazy.org). GH in this context represents Glycoside Hydrolase Family. Known mannanases belonging to GH include mannanases derived from filamentous fungi such as those belonging to the genus *Aspergillus* typically including *Aspergillus niger; Trichoderma reesei*; bacteria of the genus *Bacillus*, and the like.

The mannanase disclosed herein does not belong to the GH family to which conventional mannanases belong, and is believed to belong to a novel GH family. The substrate for the mannanase disclosed herein may be any polymers having a 1,4-β-mannoside linkage without particular limitation and may mainly be glucomannan, galactomannan and galactoglucomannan.

(Mannanase Activity Assay)

Mannanase activity may be measured by, for example, the dinitrosalicylic acid method (DNS method). Mannan is mixed with mannanase to allow reaction under certain conditions and decomposition of mannan. With regard to the reaction conditions, glucomannan at, for example, 0.2% to 2.0 is mixed with mannanase so as to obtain a final concentration of 0.5% to allow reaction at 37° C. The reaction time may be such a duration that the decomposition reaction approximately completes or an aliquot of the reaction solution may be collected at one or more time points between the initiation of the reaction and the time at which the decomposition reaction approximately completes. After completion of the decomposition reaction, the reducing sugar is quantified according to the DNS method. By quantifying the reducing sugar, mannan decomposing activity of mannanase may be assayed.

The DNS method is specifically described. By allowing dinitrosalicylic acid to react with a reducing sugar, dinitrosalicylic acid which is yellow is reduced to produce red 3-amino-5-nitrosalicylic acid. As an increase in the absorbance at 500 to 540 nm upon this production is proportional to an increase of the reducing sugar, the measurement of the absorbance allows quantification of the reducing sugar.

Alternatively, mannanase activity may be measured, for example, by thin-layer chromatography (TLC). Mannan is mixed with mannanase to allow reaction under certain conditions and decomposition of mannan. The reaction conditions are as described above. After completion of the decomposition reaction, the produced mannan decomposed products may be detected by TLC. TLC allows detection of the size of molecules of mannan decomposed products, enabling to ascertain that mannan decomposed products are those decomposed to a disaccharide mannobiose or a trisaccharide mannotriose, for example.

(Mannan)

Mannan is a collective term for polysaccharides mainly containing mannose. Mannan is a type of hemicellulose generally present in large quantity in yeasts, fungi, seeds and fruits of plants and ligneous tissue of softwood.

Known mannans include glucomannan, galactoglucomannan, galactomannan, β-mannan and the like. Glucomannan is made up of glucose and mannose coupled via a 1,4-β-mannoside linkage. For example, glucomannans in which glucose and mannose are coupled at a ratio of about 2:3 are abundantly contained in softwood and the konjac plant. Glucomannan contains in side chains thereof galactose coupled via an α-1,6 linkage and those containing galactose at a high proportion are referred to as galactoglucomannan. Galactomannan is made up of mannose having 1,4-β-mannoside linkages and galactose bound as side chains thereof via a 1,6-α-mannoside, linkage, and the proportion of galactose varies according to plants containing galactomannan. Galactomannan is abundantly contained in guar gum and coffee beans. β-mannan is made up of mannose coupled via β-1,4 linkages.

(First Mannanase)

One of mannanases disclosed herein may be a polypeptide having an amino acid sequence of SEQ ID NO: 2. Another aspect of the amino acid sequence of the polypeptide may have one or more amino acid mutations in the amino acid sequence of SEQ ID NO: 2. The number of amino acid mutations is not particularly limited and may be, for example, about 1 to 50, preferably 1 to 40, more preferably 1 to 30, more preferably 1 to 20, more preferably 1 to 10, still more preferably 1 to 5 and particularly preferably 1 or 2. The amino acid mutation may be any of substitution, deletion and addition and two or more types of mutations may be simultaneously included. A preferable example of the amino acid substitution is conservative substitution and specific substitutions included are substitutions within the respective groups as follows: (glycine, alanine) (valine, isoleucine, leucine) (aspartic acid, glutamic acid) (asparagine, glutamine) (serine, threonine) (lysine, arginine) (phenylalanine, tyrosine).

Another aspect of the polypeptide may be a polypeptide having an amino acid sequence which has 60% or more identity with the amino acid sequence SEQ ID NO: 2 and having mannanase activity. The identity is preferably 65% or more, more preferably 70% or more, still more preferably 75% or more, more preferably 80% or more, more preferably 85% or more, still more preferably 90% or more and yet more preferably 95% or more. The identity is yet further preferably 98% or more and the most preferably 99% or more.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as Similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

Another aspect of the polypeptide may be a polypeptide encoded by DNA, which, under stringent conditions, hybridizes to DNA comprising a base sequence encoding the amino acid sequence of SEQ ID NO: 2 or a complementary base sequence thereof having mannanase activity. An example of a base sequence encoding a polypeptide consisting of the amino acid sequence of SEQ ID NO: 2 is the base sequence of SEQ ID NO: 1.

Stringent condition in hybridization refers to conditions, for example in which so-called specific hybrid is formed, a non-specific hybrid is not formed. Such Stringent condition is known to those skilled in the art, for example, those skilled in the art can determine the conditions based on Molecular Cloning (Third Edition, Cold Spring Harbor Laboratory Press, New York) or Current protocols in molecular biology (edited by Frederick M. Ausubel et al., 1987). For example, stringent conditions include those nucleic acid having high identity such as DNAs or their complementary DNA having 60% or more, more preferably 65% or more, still more preferably 70% or more, more preferably 75% or more, still more preferably 80% or more, still more preferably 90% or more, yet more preferably 95% or more, yet further preferably 98% or more and the most preferably 99% or more identity with a base sequence of SEQ ID NO: 1 can hybrydize while nucleic acid having lower identity cannot hybridize. Typically, Na salt concentration is 15 to 750 mM, preferably 50 to 750 mM, more preferably 300 to 750 mM, temperature is 25 to 70 deg C., preferably 50 to 70 deg C., more preferably 55 to 65, and formamide concentration is 0 to 50%, preferably 20 to 50%, more preferably 35 to 45%. Further, stringent condition includes filter washing condition after hybridization which Na salt concentration is 15 to 600 mM, preferably 50 to 600 mM, more preferably 300 to 600 mM and temperature is 50 to 70 deg C., preferably 55 to 70 deg C., more preferably 60 to 65 deg C., typically.

As a stringent condition, for example, hybridization solution (50% formamide, 10×SSC (0.15 M NaCl, 15 mM sodium citrate, pH 7.0), 5×Denhardt solution, 1% SDS, 10% dextran sulfate, 10 µg/ml Of denatured salmon sperm DNA, 50 mM phosphate buffer (pH 7.5)) at about 42° C. to about 50° C. and then incubated at about 65° C. using about 0.1×SSC, 0.1% SDS at about 65° C. Conditions for washing at 70° C. can be mentioned. More preferable stringent conditions include, for example, 50% formamide, 5×SSC (0.15 M NaCl, 15 mM sodium citrate, pH 7.0), 1×Denhardt solution, 1% SDS, 10% dextran sulfate, 10 µg/Ml denatured salmon sperm DNA, 50 mM phosphate buffer (pH 7.5).

Another aspect of the polypeptide may be a polypeptide encoded by DNA having a base sequence which has 60% or more, more preferably 65% or more, still more preferably 70% or more, more preferably 75% or more, still more preferably 80% or more, more preferably 85% or more, still more preferably 90% or more, yet more preferably 95% or more, yet further preferably 98% or more and the most preferably 99% or more identity with a base sequence of SEQ ID NO: 1 and having mannanase activity. An example of a base sequence encoding a polypeptide consisting of the amino acid sequence of SEQ ID NO: 2 is the base sequence of SEQ ID NO: 1.

It is sufficient that the polypeptides according to such aspects have mannanase activity at any level. The activity is preferably 20% or more, preferably 30% or more, more preferably 40% or more, still more preferably 50% or more, yet more preferably 60% or more, yet further preferably 70% or more, still further preferably 80% or more, the most preferably 90% or more and still the most preferably 100% or more of mannanase activity of the polypeptide consisting of the amino acid sequence of SEQ ID NO: 2.

The mannanase consisting of the amino acid sequence of SEQ ID NO: 2 may have a substrate of hemicellulose or a low molecule mannooligosaccharide of pentasaccharide or above, provided that the substrate has a 1,4-β-mannoside linkage. Examples of the mannooligosaccharide include mannopentaose, mannohexaose and the like.

The mannanase is preferably terminated with an amino acid sequence at the C-terminus. It is preferable that the C-terminus does not have a tag and the like added thereto and it is preferable that the C-terminus does not have at least a histidine tag added thereto.

To look into characteristics of the mannanase on mannan such as the substrate specificity and molecular activity, Km, Kcat and a Kcat/Km ratio, for example, may be calculated. The mannanase disclosed herein, for example, has Km on glucomannan of 1.2 mg/ml, Kcat of 390 s$^{-1}$ and Kcat/Km of 330 ml$^{-1}$s$^{-1}$ mM. The mannanase has Km on galactomannan of 4.7 mg/ml, Kcat of 240 s$^{-1}$ and Kcat/Km of 51 ml$^{-1}$s$^{-1}$ mM, Km, Kcat and the Kcat/Km ratio may be calculated according to well-known methods.

The mannanase preferably has an optimal pH of pH 5 or more and pH 7 or less and more preferably pH 5.5 or more and pH 6.5 or less. A well-known mannanase derived from *A. nidulans* (rMan5) has an optimal pH of pH 3 or more and pH 5 or less and the most preferably about 4.

The mannanase preferably has such heat resistance that the proportion (%) of activity relative to the enzyme activity at 20° C. is 60% or more at 60° C., more preferably 60% or more at 70° C., still more preferably 60% or more at 80° C. and yet more preferably 60% or more at 90° C. It is also preferable that the heat resistance is such that the proportion of activity relative to the enzyme activity at 50° C. is 65% or more at 60° C., more preferably 65% or more at 70° C. still more preferably 65% or more at 80° C. and yet more preferably 65% or more at 90° C. For example, rMan5 has the proportion of activity relative to the enzyme activity at 20° C. of 60% or less at 70° C. and 10% or less at 80° C. The proportion of activity relative to the enzyme activity at 50° C. is 65% or less at 70° C. and 10% or less at 80° C. It should be noted that the enzyme activity is measured under the same conditions other than the temperature.

The first mannanase may be obtained from a culture supernatant after culturing *A. nidulans* in a glucomannan medium.

Second to fifth mannanases are hereinafter described. The mannanases are, similar to the first mannanase, endoenzymes hydrolyzing 1,4-β-mannoside linkages of mannan and also referred to as β-mannanase and β-mannosidase. According to the EC classification of enzymes, the mannanases may be classified into EC3.2.1.78. It is also believed that the mannanases belong to a novel GH family together with the first mannanase, rather than the known GH family to which existing mannanases belong.

The mannanases may also have substrates, similar to the first mannanase, which are mannan, hemicellulose provided that the hemicellulose has a 1,4-β-mannoside linkage and low molecule mannooligosaccharides of pentasaccharides, hexasaccharides or above. Examples of the mannooligosaccharides include mannopentaose, mannohexaose and the like. The mannanases also preferably terminated with amino acid sequences at the C-termini. It is preferable that the C-terminus does not have a tag or the like added thereto and it is preferable that the C-terminus does not have at least a His-tag added thereto.

(Second and Third Mannanases)

The disclosure herein also relates to other novel mannanases derived from *A. nidulans* (hereinafter referred to as second and third mannanases) and use thereof. The mannanases may be regarded as homologues of the first mannanase. The proteins corresponding to the second and third mannanases may be obtained from a culture supernatant after culturing *A. nidulans* in a glucomannan medium.

The second mannanase preferably has an optimal pH of pH 4.5 or more and pH 6.5 or less. The third mannanase preferably has an optimal pH of pH 4.5 or more and pH 6.5 or less.

The second and third mannanases may be polypeptides having amino acid sequences of SEQ ID NOs: 4 and 6, respectively. The amino acid sequence of SEQ ID NO: 4 has 70% identity with the amino acid sequence of SEQ ID NO: 2 which may define the first mannanase. The amino acid sequence of SEQ ID NO: 6 has 54% identity with the amino acid sequence of SEQ ID NO: 2.

Other aspects of the polypeptide which may be of the second mannanase include, similar to other aspects of amino acid sequences for the first mannanase, various aspects based on the amino acid sequence of SEQ ID NO: 4 and a base sequence of SEQ H) NO: 3 encoding the amino acid sequence. Other aspects of the polypeptide which may be of the third mannanase include, similar to other aspects of amino acid sequences for the first mannanase, various aspects based on the amino acid sequence of SEQ ID NO: 6 and a base sequence of SEQ ID NO: 5 encoding the amino acid sequence.

(Fourth Mannanase)

The disclosure herein also related to a novel mannanase derived from *A. oryzae* (hereinafter referred to as fourth mannanase) and use thereof. The protein corresponding to the fourth mannanase may be obtained from a culture supernatant after culturing *A. oryzae* in a glucomannan medium.

The fourth mannanase may be a polypeptide having an amino acid sequence of SEQ ID NO: 8. The amino acid sequence of SEQ ID NO: 8 has 71% identity with the amino acid sequence of SEQ ID NO: 2 which may define the above mannanase.

To look into characteristics of the fourth mannanase on mannan such as the substrate specificity and molecular activity, Km, Kcat and a Kcat/Km ratio, for example, may be calculated. The fourth mannanase, for example, has Km on glucomannan of 1.8±0.2 mg/ml, Kcat of 590/sec and Kcat/Km of 330 ml/mg·sec. The mannanase also has Km on galactomannan of 5.1±0.4 mg/ml, Kcat of 290/sec and Kcat/Km of 57 ml/mg·sec.

The fourth mannanase preferably has an optimal pH of pH 4 or more and pH 7 or less and more preferably pH 4.5 or more and pH 6.5 or less.

The fourth mannanase preferably has such heat resistance that the proportion (%) of activity relative to the enzyme activity at 37° C. of 70% or more at 60° C., more preferably 70% or more at 70° C. and still more preferably 60% or more at 80° C.

Other aspects of the polypeptide which may be of the fourth mannanase include, similar to other aspects of amino acid sequences for the above mannanases, various aspects based on the amino acid sequence of SEQ ID NO: 8 and a base sequence of SEQ ID NO: 7 encoding the amino acid sequence.

Examples of proteins of *A. oryzae* having high identity with the amino acid sequence of SEQ ID NO: 8 of the fourth mannanase include an amino acid sequence of SEQ ID NO: 12 (the base sequence of DNA encoding the amino acid sequence is SEQ ID NO: 11).

(Fifth Mannanase)

The disclosure herein further relates to a novel mannanase derived from *Streptomyces*, sp (hereinafter referred to as fifth mannanase) and use thereof. The protein corresponding to the fifth mannanase was obtained by synthesizing a DNA sequence encoding the amino acid sequence of WP_030268297.1 which is registered at NCBI, and ligating the same to pET28a to construct a plasmid, which was used to transform *E. coli* BL21 CodonPlus in order to express the protein.

The fifth mannanase may be a polypeptide having an amino acid sequence of SEQ ID NO: 10. The amino acid sequence of SEQ ID NO: 10 has 61% identity with the amino acid sequence of SEQ ID NO: 2 which may define the first mannanase.

The fifth mannanase preferably has an optimal pH of pH 4 or more and pH 7 or less and more preferably pH 4.5 or more and pH 6.5 or less.

Other aspects of the polypeptide which may be of the fifth mannanase include, similar to other aspects of amino acid sequences for the above mannanases, various aspects based on the amino acid sequence of SEQ ID NO: 10 and a base sequence of SEQ ID NO: 9 encoding the amino acid sequence.

The first to fifth mannanases may have the following relationship with the amino acid sequence of SEQ ID NO: 2, which is the amino acid sequence of the first mannanase. Namely, the mannanases, when aligned with the amino acid sequence of SEQ ID NO: 2, have polypeptides having amino acid sequences which contain a first motif consisting of WFAGITRNGXSG (wherein X represents any amino acid) corresponding to positions 138 to 148 in the amino acid sequence, a second motif consisting of DLAI/VAMLE corresponding to positions 54 to 61 in the amino acid sequence, a third motif consisting of NFGI/LFKQNW corresponding to positions 81 to 89 in the amino acid sequence and DTRFWVX$_1$VX$_2$AI (wherein X$_1$ and X$_2$ represent any amino acid) corresponding to positions 181 to 191 in the amino acid sequence, and have 54% or more identity with the amino acid sequence of SEQ ID NO: 2.

There is no specific limitation to the alignment of the amino acid sequences, and, for example, the alignment of the amino acid sequences may be carried out by various well-known programs. Examples of such programs include BLAST (blast.ncbi.nlm.nih.gov/Blast.cgi), Clustal W (www.genome.jp/tools/clustalw), PROSITE (prosite.expasy.org) and PRINTS (bioinf.man.ac.uk/dbbrowser/PRINTS/PRINTS.html), ProDOM (prodom.prabi.fr/prodom/current/html/home.php), Pfam (www.sangetac.uk/science/tools) as well as other commercially available programs. A person skilled in the art can appropriately obtain an alignment program from public websites such as NCBI, NIH, DDBJ and EBI or use the program on the website or use a commercially available alignment program to align an amino acid sequence—a comparison object—with the amino acid sequence of SEQ ID NO: 2. Alignment allows identification of an amino acid or a partial amino acid sequence in the amino acid sequence to be compared relative to one amino acid or a partial amino acid sequence consisting of two or more amino acids on the amino acid sequence of SEQ ID NO: 2.

X in the first motif is not particularly limited and may be a natural amino acid or a non-natural amino acid. X is preferably a hydrophobic amino acid such as alanine, valine, leucine, isoleucine, proline, phenylalanine, methionine and glycine and is preferably alanine. X may alternatively be a polar negatively-charged amino acid such as glutamic acid or aspartic acid or cysteine or tyrosine and is preferably glutamic acid or aspartic acid.

$X_1$ in the fourth motif is not particularly limited and may be a natural amino acid or a non-natural amino acid. $X_1$ is preferably aspartic acid, glutamic acid, tyrosine or cysteine or asparagine, glutamine, threonine or serine. $X_1$ is more preferably aspartic acid, asparagine or glutamine.

$X_2$ in the fourth motif is not particularly limited and may be a natural amino acid or a non-natural amino acid. $X_2$ is preferably glutamine, asparagine, threonine or serine or arginine, lysine or histidine and preferably glutamine, histidine or arginine. $X_2$ is alternatively valine, proline, alanine, glycine, leucine, isoleucine, tryptophan, methionine or phenylalanine and preferably valine or proline.

The first to fifth mannanases may also have the following relationships with the amino acid sequence of SEQ ID NO: 2. Namely, the mannanases may have amino acid sequences containing, when aligned with the amino acid sequence of SEQ ID NO: 2, amino acids corresponding to amino acids of positions 27 (R), 31 (G), 34 (T), 37 to 39 (GLG), 41 and 42 (RK), 48 to 50 (AGG), 65 (M), 69 (Y), 71 to 73 (YGD), 75 (K), 78 (D), 92 and 93 (LR), 117 (S), 122 and 123 (DV), 133 and 134 (YG), 152 (P), 154 (T), 156 and 157 (DI), 160 (Y), 163 and 164 (AV), 166 and 167 (WI) and 170 (Q) in the amino acid sequence of SEQ ID NO: 2.

Further, the first to fifth mannanases preferably have, when aligned with the amino acid sequence of SEQ ID NO: 2, glutamic acids corresponding to those at positions 61 and 63 in the amino acid sequence of SEQ ID NO: 2. it is believed that the glutamic acids affect mannanase activity.

For example, the first mannanase preferably has an amino acid sequence having, in addition to the above motifs and specific amino acids, 90% or more and preferably 95% or more identity with the amino acid sequence of SEQ ID NO: 2. The second mannanase preferably has an amino acid sequence having 90% or more and preferably 95% or more identity with the amino acid sequence of SEQ ID NO: 4. The third mannanase preferably has an amino acid sequence having 90% or more and preferably 95% or more identity with the amino acid sequence of SEQ ID NO: 6. The fourth mannanase preferably has an amino acid sequence having 90% or more and preferably 95% or more identity with the amino acid sequence of SEQ ID NO: 8. The fifth mannanase preferably has an amino acid sequence having 90% or more and preferably 95% or more identity with the amino acid sequence of SEQ ID NO: 10.

The polypeptides (hereinafter merely referred to as the present polypeptides) which may be of the first to fifth mannanases disclosed herein may be purified by an isolation technique such as gel electrophoresis or may be crude or partially purified with which other proteins and the like coexist. The polypeptide which is crude or partially purified may be a culture supernatant of a transformant producing the present polypeptide by secretion as described hereinbelow or a partially purified product thereof. Any method may be used for producing the present polypeptide without particular limitation. The method for producing the present polypeptide is specifically described hereinbelow.

The present polypeptide may be used as a mannanase formulation. Again, when used as a mannanase formulation, any method may be used for producing the present polypeptide without particular limitation, similar to those described above, and the polypeptide may be purified by various isolation techniques or may be crude or partially purified.

(Polynucleotide Encoding the Present Polypeptide)

A polynucleotide disclosed herein (hereinafter referred to as the present polynucleotide) encodes the present polypeptide. The present polynucleotide may include a polynucleotide encoding the present polypeptide having mannanase activity. The present polynucleotide encompasses base sequences of multiple aspects generated by genetic codon degeneracy for each amino acid. The polynucleotide may be DNA (single strand or double strand), RNA (single strand), a DNA/RNA hybrid (a hybrid of DNA single strand and RNA single strand) or a chimera of DNA and RNA. The present polynucleotide may have only a coding sequence of the present polypeptide such as cDNA or contain one or more introns such as genome as far as the polynucleotide is translated into the corresponding present polypeptide in a predetermined host.

The present polynucleotide may be obtained as a fragment by, for example, carrying out PCR amplification with primers designed based on a base sequence encoding the present polynucleotide and a polynucleotide template such as DNA extracted from A. nidulans, the natural origin of the present polypeptide or cDNA libraries or genomic DNA libraries of other various organisms. A polynucleotide fragment may also be obtained by hybridization with the above polynucleotide template derived from the libraries and the like and a probe which is a DNA fragment, namely a partial DNA encoding the present polypeptide. Alternatively, the present polynucleotide may be synthesized as a DNA fragment or the like according to various nucleic acid sequence synthesis methods well known in the art such as chemical synthesis. Further, the present polynucleotide such as DNA encoding a polypeptide having a mutation in the amino acid sequence of SEQ ID NO: 2, 4, 6, 8 or 10 is obtained by a well-known method for introducing a mutation in an amino acid sequence. The method for introducing a mutation is specifically described hereinbelow. A person skilled in the art can obtain the present polynucleotide of various aspects based on base sequences and the like described for the present polypeptide by referring to, for example, Molecular Cloning or Current protocols in Molecular Biology, supra.

(Expression Vector and Transformant)

A polynucleotide construct disclosed herein contains the present polynucleotide and, preferably, may further contain one or more elements for expressing a polypeptide encoded by the present polynucleotide in a host cell. The element is appropriately selected based on a well-known technique and examples thereof include a promoter, a terminator, a poly-A sequence, a signal peptide sequence, a homologous sequence for genome integration by homologous recombination with a host genome or the like. The polynucleotide construct may also contain a marker for selection of a transformed host cell. The polynucleotide construct may be a cyclic or linear DNA molecule or typically be in the form of an expression vector. The expression vector and a method for constructing thereof are disclosed in, for example, Molecular Cloning or Current protocols in Molecular Biology, supra and well known to those skilled in the art. The vector may be in any form according to the mode of use.

The polynucleotide construct may be introduced into a host cell by various well-known methods such as transformation, transfection, conjugation, protoplast method, electroporation, lipofection and lithium acetate method by appropriately referring to the methods disclosed in, for example, Molecular Cloning or Current protocols in Molecular Biology, supra.

The present polypeptide containing a point mutation or the like introduced in the amino acid sequence of SEQ ID NO: 2, 4, 6, 8 or 10 may be obtained by carrying out modification according to conventional mutagenesis, site directed mutagenesis, molecular evolutionary procedures using error-prone PCR and the like. Such a procedure may include well-known methods such as the Kunkel method or the Gapped duplex method and methods adapted therefrom. A mutation may be introduced by using, for example, a mutation introduction kit utilizing site directed mutagenesis (such as Mutant-K (manufactured by Takara Bio Inc.) or Mutant-G (manufactured by Takara Bio Inc.)) or a kit of LA PCR in vitro Mutagenesis series available from Takara Bio The transformant host is not particularly limited and may be any of various prokaryotic microorganisms and eukaryotic microorganisms. The prokaryotic microorganisms and eukaryotic microorganisms are not particularly limited as of the species thereof, and are preferably microorganisms for which genetic recombination technique has been established and particularly preferably a yeast or *E. coli*.

(Method for Producing a Decomposed Product from Mannan)

The method for producing a decomposed product from mannan disclosed herein include the step of decomposing mannan with the present polypeptide.

Mannan to be decomposed in the present method may be in any form without particular limitation. Mannan may be lignocellulosic or other biomass (non-edible materials) which may contain mannan. Mannan may be hemicellulosic materials isolated from such biomass materials. Mannan may be partially or completely purified. Mannan may be edible materials containing mannan. Examples of the edible materials include various fruits, coffee beans, taros and yams and processed foods thereof such as konjac and jellies.

EMBODIMENTS

The present invention is hereinafter specifically described by way of Embodiments which do not limit the present invention.

First Embodiment (Identification of a Hypothetical Protein)
In the present Embodiment, a hypothetical protein was identified from a culture supernatant after culturing *A. nidulans* in a glucomannan medium. A liquid medium (a minimal medium containing glucomannan as a sole carbon source: glucomannan medium) containing glucomannan at a final concentration of 1.0% was prepared in a 500-ml conical flask. A suspension (500 µl) of spores of wild-type (WT) of which number of spores were adjusted (2,000 spores per µl) by using a counting chamber was inoculated therein. Shake culture was carried out at 30° C. for 24 hours (100 rpm) and cells were separated from the culture solution by using a Buchner funnel. The filtered culture solution thus recovered was concentrated to 25 ml with Vivaspin and 1 ml of the solution was used for TCA precipitation. The precipitated proteins were washed with acetone, dissolved in a sample buffer, subjected to SDS-PAGE (acrylamide gel concentration: 15%) in which electrophoresis was carried out under a constant current condition (20 mA) followed by Coomassie staining. The result of the SDS-PAGE is shown in FIG. 1. After staining, bands were excised and proteins were treated with trypsin followed by analysis on MALDI-TOF/TOF-MS. The obtained data (peptide fingerprinting and MS/MS spectrum) were used for MASCOT search in order to identify the protein, which resulted in identification of a hypothetical protein (HP) which was extracellularly secreted in large quantity in the similar manner as endo-1,4-β-mannanase, as shown in No. 7 in the table in FIG. 1.

(Purification of Recombinant HP and Recombinant Man5)

RNA was extracted from *Aspergillus nidulans* grown solely on a carbon source of glucomannan by using RNeasy Plant Mini Kit (Qiagen N.V.) and reverse-transcribed with PrimeScript™ 1st cDNA Synthesis Kit (TaKaRa) to obtain cDNA. PCR was carried out with the synthesized cDNA as a template and a primer A (5'-CCCAAGCTTCGGC-CCCCACGACGGACATGACCA-3') (SEQ ID NO: 13) and a primer B (5'-CCGCTCGAGTTAGATAGCCTGGACAT-CAACCCAAAAGCG-3') (SEQ ID NO: 14) to amplify the HP gene. After the PCR product was subjected to agarose gel electrophoresis, the fragment of the desired gene was excised and DNA was extracted and purified from agarose gel with UltraClean® 15 DNA Purification Kit (MO BIO Laboratories, Inc.). After treating with restriction enzymes, the fragment was ligated to pET28a to construct a plasmid for HP expression. *E. coli* BL21 CodonPlus was transformed with the plasmid to obtain *E. coli* for HP expression.

Figure 2:
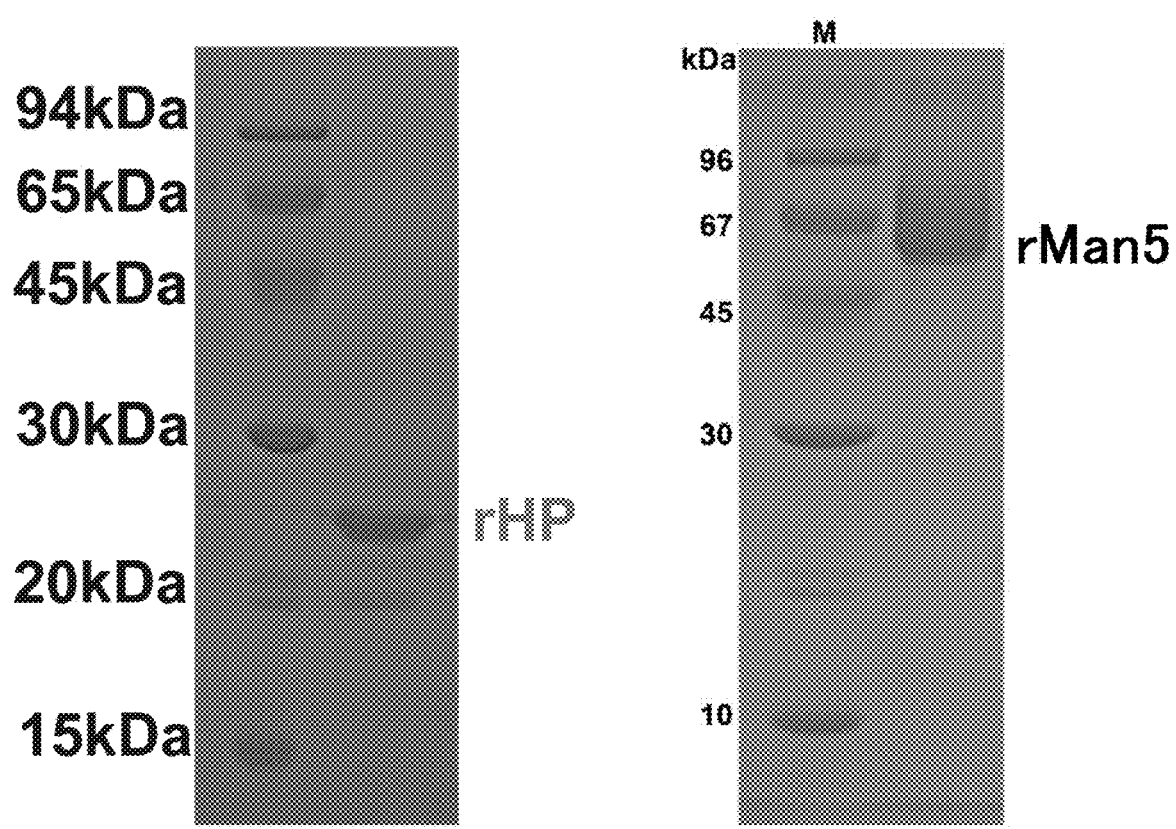
FIG. 2 shows SDS-PAGE analysis of purified rHP and rMan5.

In a test tube containing 5 ml of LB medium (supplemented with kanamycin and chloramphenicol), *E. coli* for HP expression was pre-cultured for 3 hours (100 rpm) and then 50 µl of the culture solution was transferred to a 300-ml conical flask containing 50 ml fresh LB medium (supplemented with kanamycin, chloramphenicol and 0.25 mM IPTG) for main culture over 8 hours. *E. coli* was recovered in a 50-ml Falcon tube and cells were collected by centrifugation. The cells were suspended in 25 ml buffer A (50 mM Tris-HCl pH 8.0, 150 mM NaCl) and disrupted by sonication. After cell disruption, the sample was centrifuged and filtered (0.22 µm) to remove insoluble matters. The sample was then applied onto an Ni-affinity column to adsorb recombinant HP (rHP) onto the column which was washed three times with buffer A and rHP was eluted with buffer A containing 300 mM imidazole, thereby being purified. The result of SDS-PAGE of purified rHP is shown in FIG. 2.

A known mannanase derived from *A. nidulans*, Man5, was produced as a recombinant Man5 (rMan5) in *P. pastris* and then purified. PCR was carried out with cDNA of *A. nidulans* and a primer C (5'-CGGGGTACCCG-CAAGGGCTTTGTGACCACCAAAGGCGA-3') (SEQ ID NO: 15) and a primer D (5'-ATAGTTTAGCGGCCGC- CTACCGTCTCCGGITTCAACTTGTT-3') (SEQ ID NO: 16) in order to amplify Man5 gene. After the PCR product was subjected to agarose gel electrophoresis, the fragment of the desired gene was excised and DNA was extracted and purified from agarose gel with UltraClean® 15 DNA Purification Kit (MO BIO Laboratories, Inc.). After treating with restriction enzymes, the fragment was ligated to pPICZα-A (Invitrogen Corporation) to construct a plasmid for Man5 expression. *Pichia pastris* KH71 was transformed with the plasmid to obtain *P. pastris* for Man5 expression.

Production of recombinant Man5 (rMan5) in *P. pastris* for Man5 expression was carried out according to the instruction attached to EasySelect™ *Pichia* Expression Kit (Invitrogen Corporation). In 3 L BMMY medium, *P. pastris* for Man5 expression was cultured and then rMan5 was purified on a DEAE-cellulose column. Upon usage in, for example, enzyme activity assay, rMan5 was dialyzed and desalted. The result of SDS-PAGE of purified rMan5 is shown in FIG. 2.

Second Embodiment (Substrate Specificity of rHP)
In the present Embodiment, the substrate specificity of rHP was examined. To each of various carbon sources at 1.0% used as substrates were added 100 μl of 100 mM sodium phosphate (pH 6.5) and 0.5 μM (final concentration) of rMan5, rHP or rHP to which a histidine tag was added to the C-terminus (rHP-CHis), and the total volume was adjusted to 500 μl with deionized water. The mixture was then incubated at 37° C. and the reducing sugar was quantified according to the DNS method. The carbon sources used were chitin, xylan, cellulose, galactomannan and glucomannan. The results are shown in FIG. 3.

Figure 4:
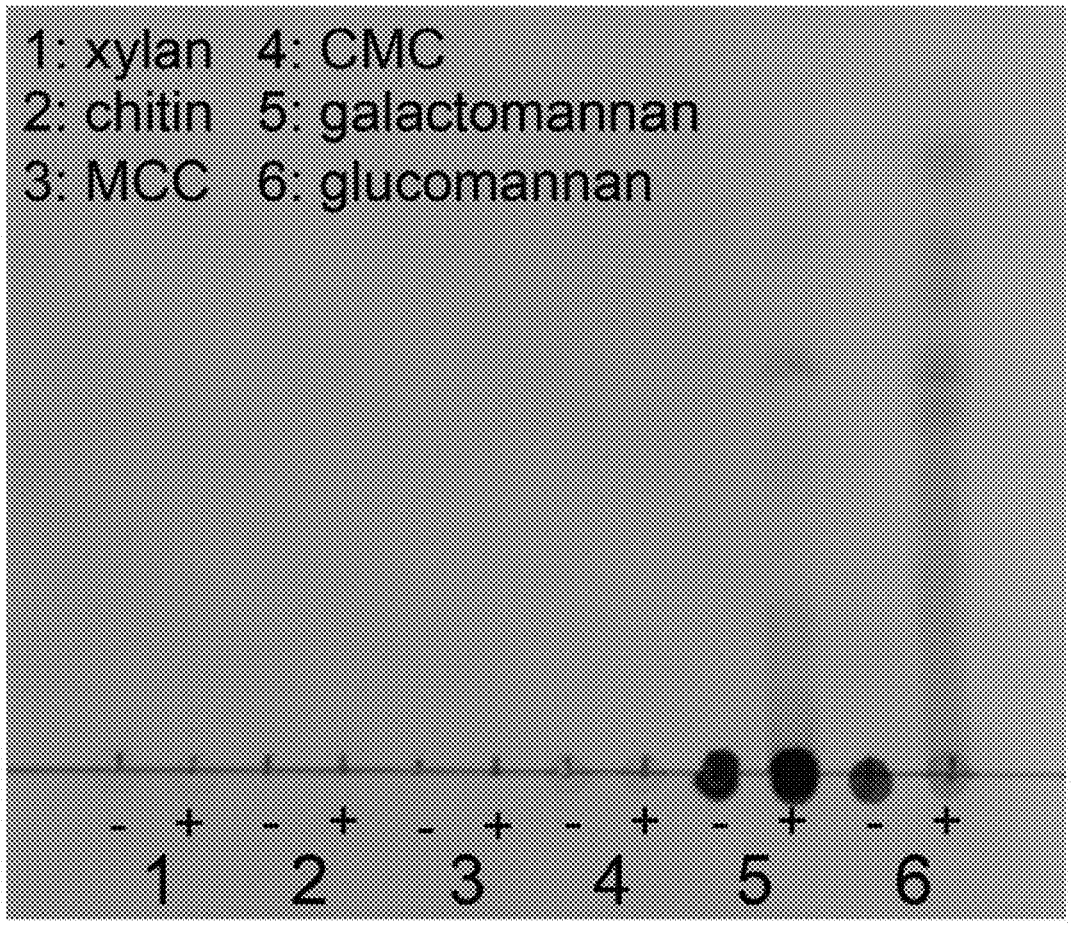
FIG. 4 shows detection of decomposed products from various carbon sources mixed with rHP.

The reaction products were verified also by TLC. The reaction solutions (1 μl each) of various carbon sources with rHP were spotted on a TLC plate and allowed to develop. The developing phase was n-butanol:ethanol:water=10:8:7. After drying completely with a dryer following the development, a color reagent was sprayed to the plate which was then further heated with a dryer for 5 minutes to detect reaction products. The color reagent used was prepared from N-(1-naphthyl)ethylenediamine dihydrochloride (8.2 g/L) and sulfuric acid (8.6%) in ethanol. The carbon sources used were xylan, chitin, microcrystalline cellulose (MCC), carboxymethylcellulose (CMC), galactomannan and glucomannan. As a control, each of the carbon sources without addition of rHP was spotted. The results are shown in FIG. 4.

Figure 3:
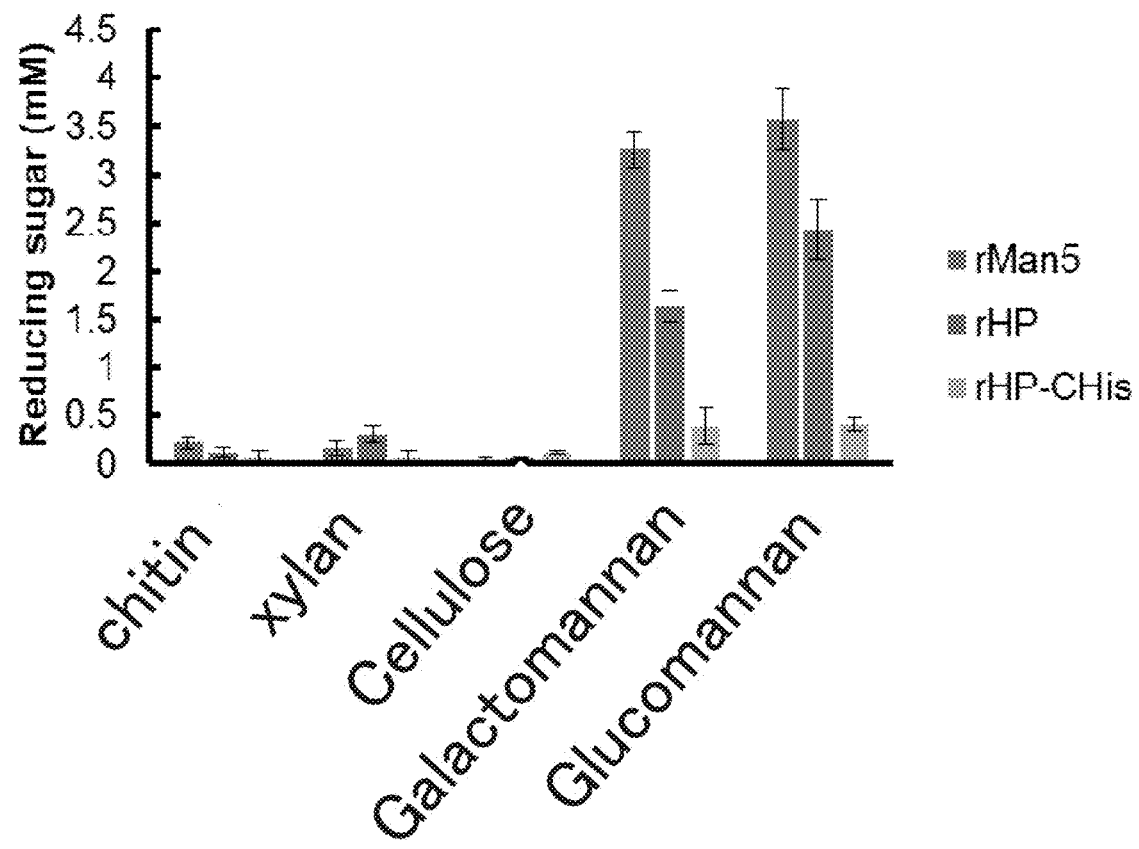
FIG. 3 shows the amount of reducing sugars produced when various carbon sources are mixed with one of rMan5, rHP and rHP-CHis.

As shown in FIG. 3, rHP, similar to rMan5, hydrolyzed galactomannan and glucomannan, but did not hydrolyze chitin, xylan and cellulose which are non-mannan carbon sources. As shown in FIG. 4, rHP hydrolyzed galactomannan and glucomannan, but did not hydrolyze xylan, chitin, MCC and CMC which are non-mannan carbon sources. The results revealed that rHP specifically hydrolyzes mannan.

Further, as shown in FIG. 3, little reducing sugar was produced from rHP-CHis galactomannan and glucomannan compared to rMan5 and rHP. The results suggest that addition of a histidine tag to rHP at the C-terminus reduces endo-1,4-β-mannanase activity.

Third Embodiment (Endo-1,4-β-Mannanase Activity of rHP)
In the present Embodiment, endo-1,4-β-mannanase activity of rHP was examined. To 1.0% glucomannan (Megazyme International) used as a substrate were added 100 μl of 100 mM sodium phosphate (pH 6.5) and 0.5 μM (final concentration) of rMan5 or rHP, and the total volume was adjusted to 500 with deionized water. The mixture was then incubated at 37° C. and the reducing sugar was quantified over time according to the DNS method to calculate endo-1,4-β-mannanase activity. The results are shown in the upper figure of FIG. 5.

The reaction products were verified also by TLC. The reaction solutions (1 μl each) of glucomannan with rMan5 and glucomannan with rHP were spotted on a TLC plate and allowed to develop. The reaction products were detected by TLC in the same manner as in Second Embodiment. In order to compare with the reaction products, controls (std) were used which were mannobiose (M2), mannotriose (M3), mannotetraose (M4), mannopentaose (M5) and mannohexaose (M6) purchased from Megazyme International. The results are shown in the lower figure of FIG. 5.

Figure 5:
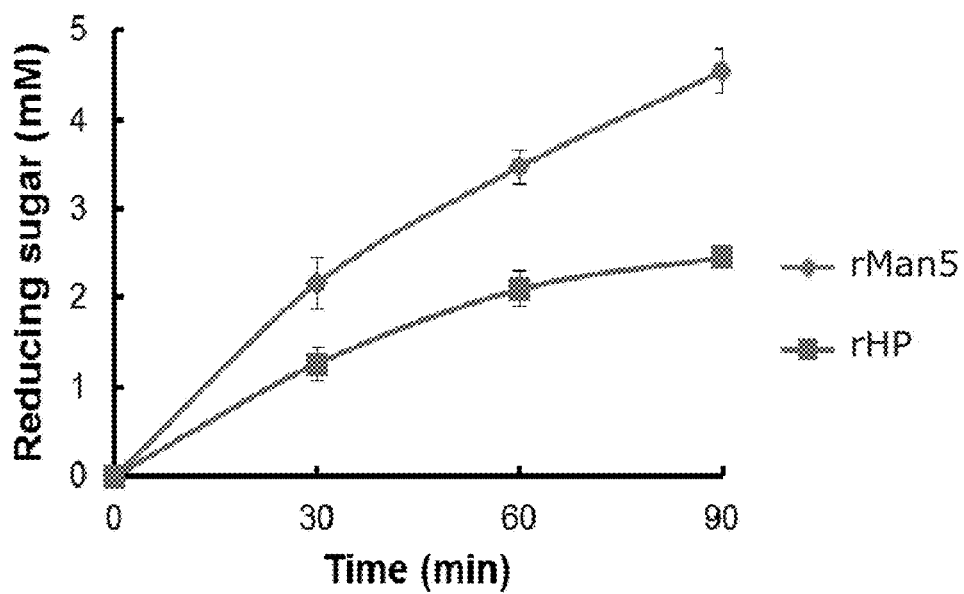
FIG. 5 shows mannanase activity of rHP, an upper figure shows the amount of the reducing sugars from glucomannan mixed with rMan5 or rHP, and a lower figure shows detection of decomposed products from glucomannan mixed with rMan5 or rHP.
Figure 5:
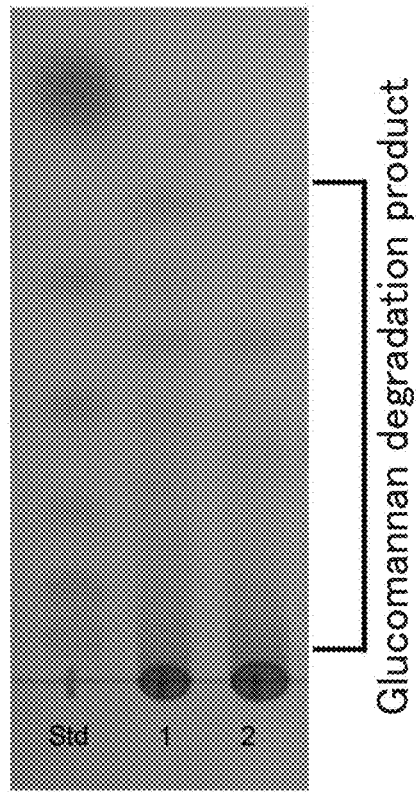

As shown in the upper and lower figures of FIG. 5, the glucomannan decomposed product from rHP exhibited a similar chromatogram as the decomposed products from rMan5 and endo-1,4-β-mannanase. The results revealed that rHP has endo-1,4-β-mannanase activity.

Fourth Embodiment (Substrate Specificity of rHP Towards Mannooligosaccharides)
In the present Embodiment, the substrate specificity of rHP towards mannooligosaccharides was examined. To 5 mM mannooligosaccharide (mannobiose (M2), mannotriose (M3), mannotetraose (M4), mannopentaose (M5) or mannohexaose (M6)) used as a substrate were added 100 μl of 100 mM sodium phosphate (pH 6.5) and 0.5 μM (final concentration) of rHP, and the total volume was adjusted to 500 μl with deionized water. The mixture was then incubated at 37° C. for 0 minutes, 5 minutes, 10 minutes, 15 minutes, 30 minutes, 45 minutes, 60 minutes and 12 hours. The reaction products were detected by TLC in the same manner as in Second and Third Embodiments. The results are shown in FIG. 6.

Decrease of the substrates and production of the reaction products were monitored by HPLC (Prominence reducing sugar analysis system, Shimadzu Corporation). The column used was Shim-pack. ISA-07/S2504 column (4.0×250 mm, Shimadzu Corporation). The eluent used for HPLC was a linear gradient of 0.1 M potassium borate buffer (pH 8.0) and 0.4 M potassium borate buffer (pH 9.0) at a flow rate of 0.6 mL min$^{-1}$ and analysis was carried out over 70 minutes. The decrease of the substrates and the production of the reaction products were quantified by using standard products thereof. The results are shown in FIG. 7.

Figure 6:
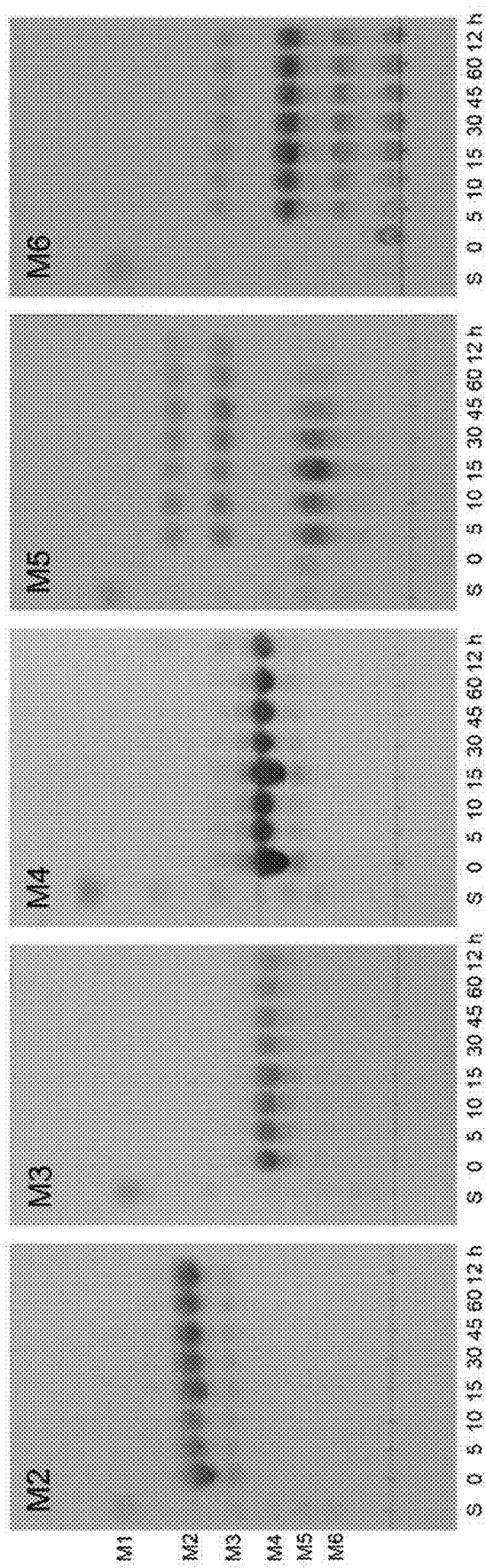
FIG. 6 shows detection of decomposed products from various mannooligosaccharides mixed with rHP.
Figure 7:
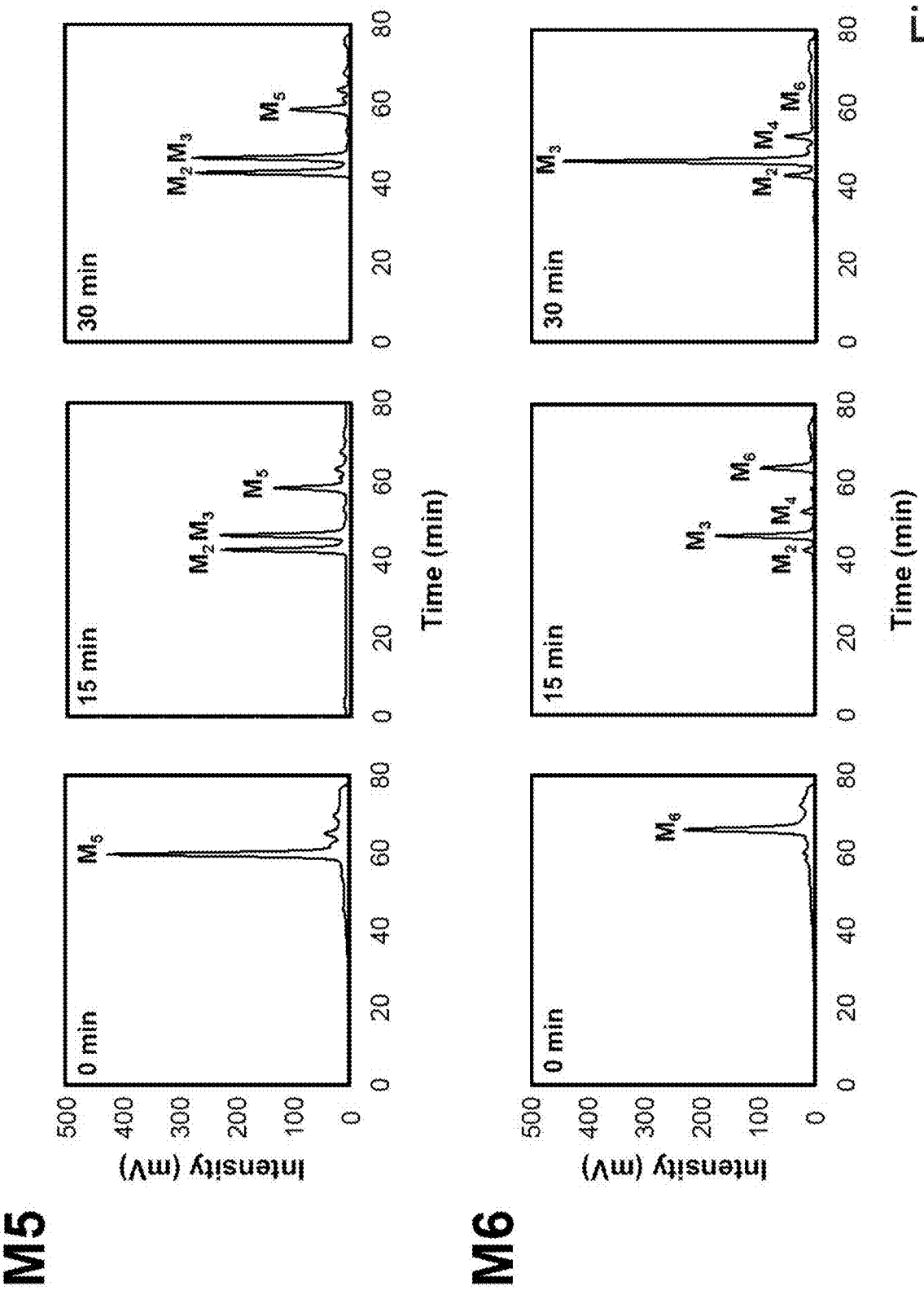
FIG. 7 shows the result of HPLC analysis of various mannooligosaccharides mixed with rHP.

As shown in FIG. 6 and FIG. 7, rHP did not hydrolyze mannobiose (M2), mannotriose (M3) or mannotetraose (M4) and hydrolyzed mannopentaose (M5) and mannohexaose (M6). As shown in FIG. 7, when the substrate was mannohexaose (M6), a large amount of mannotriose (M3) was produced as a decomposed product. The results revealed that rHP can hydrolyze a substrate which is a mannooligosaccharide of pentasaccharide or above.

Fifth Embodiment (GH Family to which HP Belongs)
In the present Embodiment, the GH family to which HP belongs was examined. BLAST search was carried out, and orthologues of HP were selected and aligned by using ClustalW. In addition, MEGA was used to generate a molecular phylogenetic tree. MEGA (Molecular Evolutionary Genetics Analysis) is a software for molecular evolutionary or phylogenetic analyses. The molecular phylogenetic tree is shown in FIG. 8.

Figure 8:
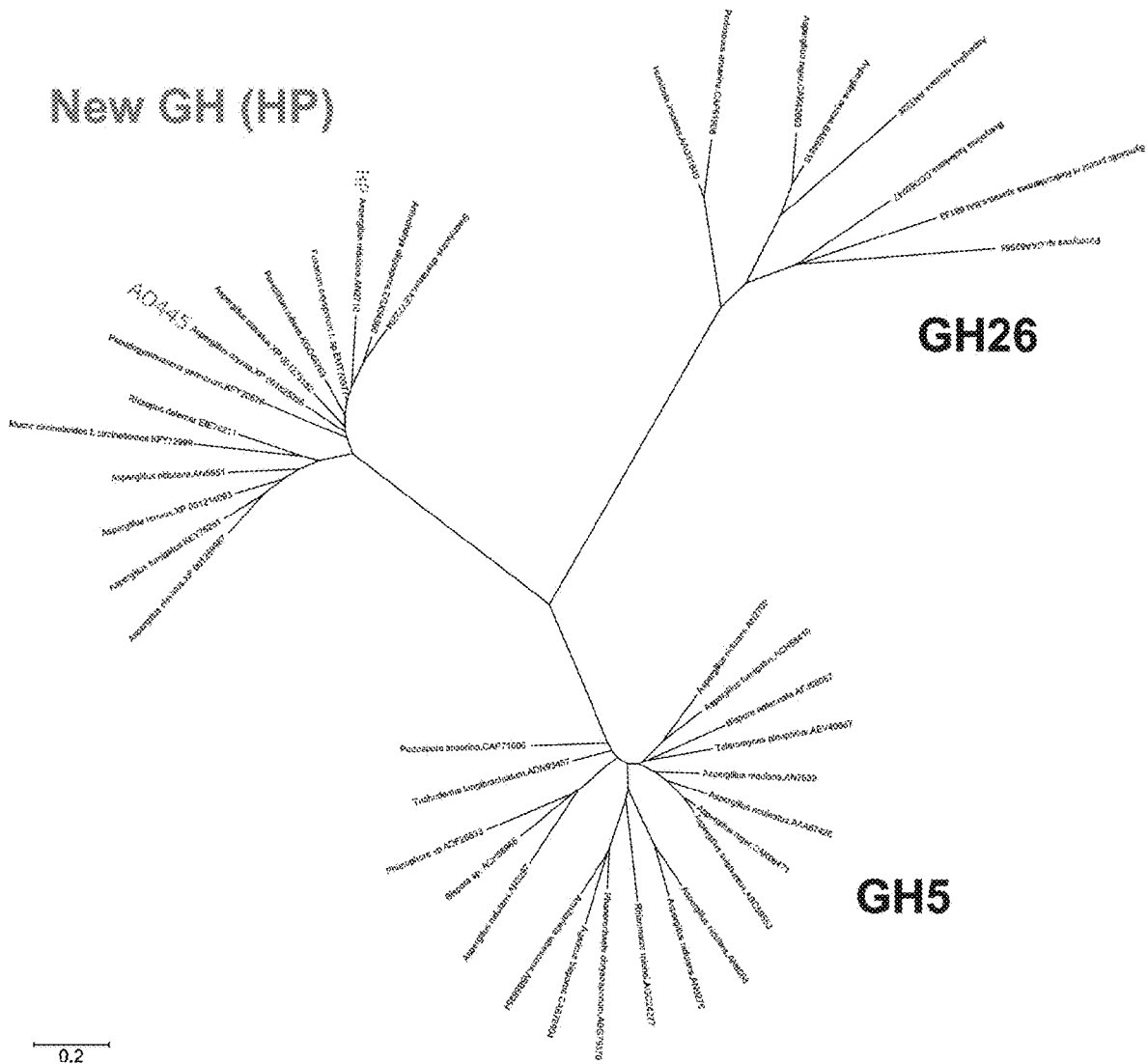
FIG. 8 shows a phylogenetic tree of rHP.

As shown in FIG. 8, it was revealed that HP does not belong to GH5 or GH26 family to which existing mannanases belong. Namely, it was suggested that HP belongs to a novel GH family.

Sixth Embodiment

In the present Embodiment, further characteristics of rHP were examined.

(Optimal pH of rHP)

The optimal pH for mannanase activity of rHP was examined. By using 1% glucomannan as a substrate, endo-1,4-β-mannanase activity was assayed in 50 mM sodium acetate (pH 3.0 to 6.0), 50 mM sodium phosphate (pH 5.0 to 7.0) and 50 mM Tris-HCl (pH 7.0 to 10.0) to determine the optimal pH of rHP and rMan5. In addition, by using a well-known method, Km, Kcat and Kcat/Km of rHP and rMan5 on glucomannan and galactomannan were calculated. The results are shown in FIG. 9.

Figure 9:
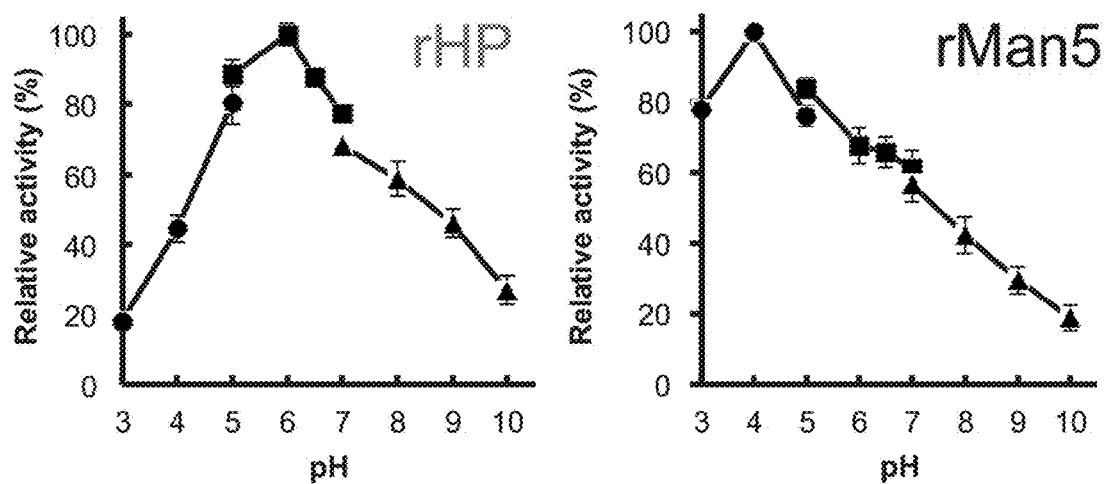
FIG. 9 shows the optimal pH of rHP on glucomannan.

As shown in FIG. 9, it was revealed that rHP has an optimal pH on glucomannan of pH 5 to 7. It was also revealed that rMan5 has an optimal pH in an acidic region of pH 3 to 5 while rHP has an optimal pH in a neutral region. It was also found that rHP had Km of 1.2 mg/ml, Kcat of 390 $s^{-1}$ and Kcat/Km of 330 $ml^{-1}s^{-1}$ mM.

(Optimal Temperature of rHP)

The optimal temperature of rHP was examined. To 1.0% glucomannan used as a substrate were added 100 μl of 100 mM sodium phosphate (pH 6.5) and 0.5 μM (final concentration) of rMan5 or rHP, and the total volume was adjusted to 500 μl with deionized water. The incubation was then carried out at 20° C. to 100° C. and the reducing sugar was quantified over time according to the DNS method to determine the optimal temperature of rHP and rMan5. The results are shown in FIG. 10.

Figure 10:
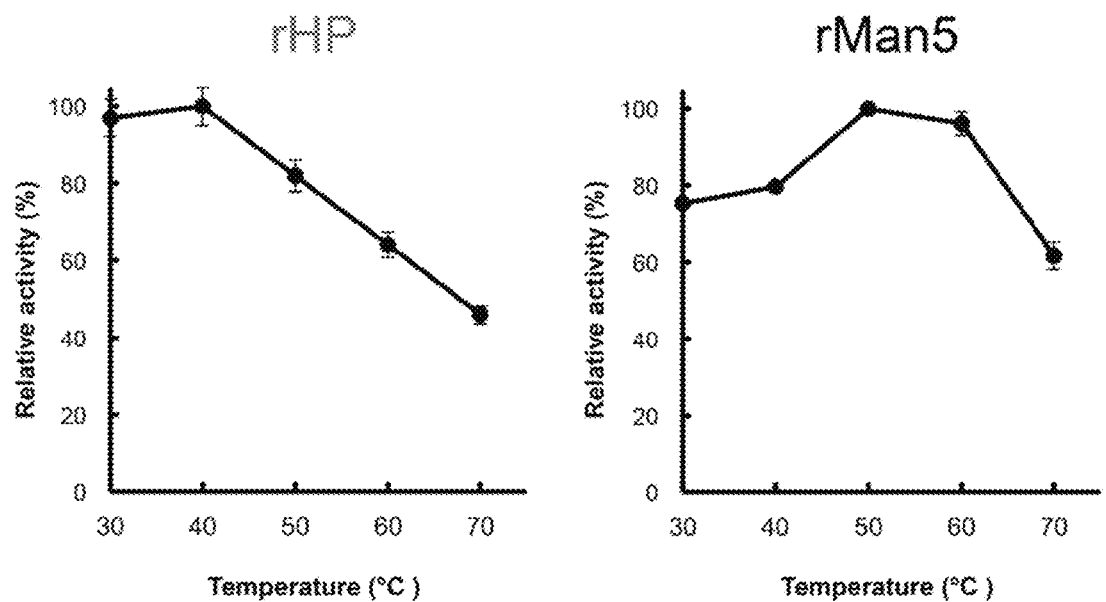
FIG. 10 shows the optimal temperature of rHP.

As shown in FIG. 10, rMan5 had an optimal temperature of about 50° C. to 60° C. while rHP had an optimal temperature of 30° C. to 40° C.

(Heat Resistance of rHP)

Heat resistance of rHP was examined. rHP or rMan5 was dissolved in 20 mM sodium phosphate (pH 6.5) solution, incubated at 20° C. to 100° C. for 15 minutes and endo-1,4-β-mannanase activity was then similarly assayed with 1.0% glucomannan used as a substrate in 20 mM sodium phosphate (pH 6.5) solution (at 37° C., thereby calculating temperature resistance of rHP and rMan5. The results are shown in FIG. 11.

Figure 11:
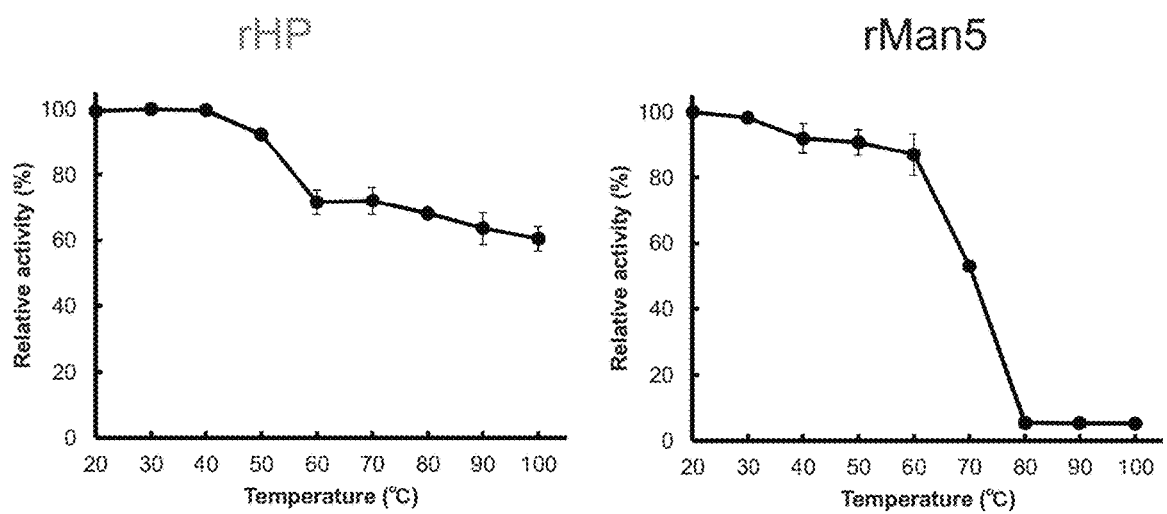
FIG. 11 shows heat resistance of rHP.

As shown in FIG. 11, rHP had activity of 80% or more at 20° C. to 50° C. and of 60% or more at 50° C. to 100° C. relative to the enzyme activity at 20° C. rMan5 had activity of 60% or less at 70° C. and of 10% or less at 80° C. or higher relative to the enzyme activity at 20° C. The results revealed that rHP has increased heat resistance compared to an existing mannanase.

Seventh Embodiment

In the present Embodiment, a protein AO445 (consisting of the amino acid sequence of SEQ ID NO: 8) was examined which has high homology at an amino acid level with HP and is derived from Aspergillus oryzae.

(Preparation of Recombinant AO445 by Utilizing the Pichia pastris Expression System)

RNA was extracted from Aspergillus nidulans grown solely on a carbon source of glucomannan by using RNeasy Plant Mini Kit (Qiagen N.V.) and reverse-transcribed with PrimeScript™ 1st cDNA Synthesis Kit (TaKaRa) to obtain cDNA. PCR was carried out with the synthesized cDNA as a template and a primer E (5'-CGGGGTACCGCTC-CAACTCCCGATGCTTCC-3') (SEQ ID NO: 17) and a primer F (5'-ATAGTTTAGCGGCCGCTTAGATGGCAC-GAACAATTGACCCAAA-3') (SEQ ID NO: 18) to amplify the AO445 gene having high homology with the HP gene. After the PCR product was subjected to agarose gel electrophoresis, the fragment of the desired gene was excised and DNA was extracted and purified from agarose gel with UltraClean® 15 DNA Purification Kit (MO BIO Laboratories, Inc.). After treating with restriction enzymes, the fragment was ligated to pPICZα-A (Invitrogen Corporation) to construct a plasmid for AO445 expression. Pichia pastris KH71 was transformed with the plasmid to obtain P. pastris for AO445 expression.

Figure 12:
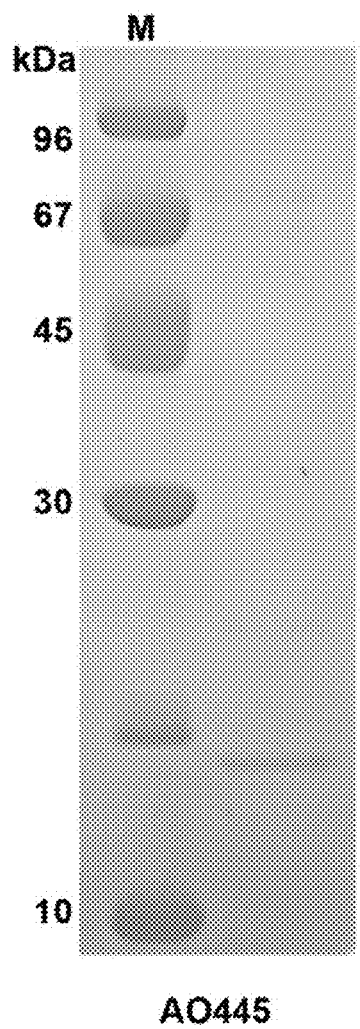
FIG. 12 shows SDS-PAGE analysis of purified rAO445.

Production of recombinant AO445 (rAO445) in P. pastris for AO445 expression was carried out according to the instruction attached to EasySelect™ Pichia Expression Kit (Invitrogen Corporation). In 3 L BMMY medium, P. pastris for AO445 expression was cultured and then rAO445 was purified on a DEAE-cellulose column. Upon usage in, for example, enzyme activity assay, rAO445 was dialyzed and desalted. The result of SDS-PAGE of purified rAO445 is shown in FIG. 12.

(Endo-1,4-β-Mannanase Activity of rAO445)

Endo-1,4-β-Mannanase activity of rAO445 was examined. To 1.0% glucomannan used as a substrate were added 100 μl of 100 mM sodium phosphate (pH 6.5) and 0.5 μM (final concentration) of rAO445 or rMan5, and the total volume was adjusted to 500 μl with deionized water. The mixture was then incubated at 37° C. The reaction products were detected by TLC in the same manner as in Second Embodiment. In order to compare with the reaction products, controls (std) were used which were mannobiose (M2), mannotriose (M3), mannotetraose (M4), mannopentaose (M5) and mannohexaose (M6) purchased from Megazyme International. The results are shown in FIG. 13.

Figure 13:
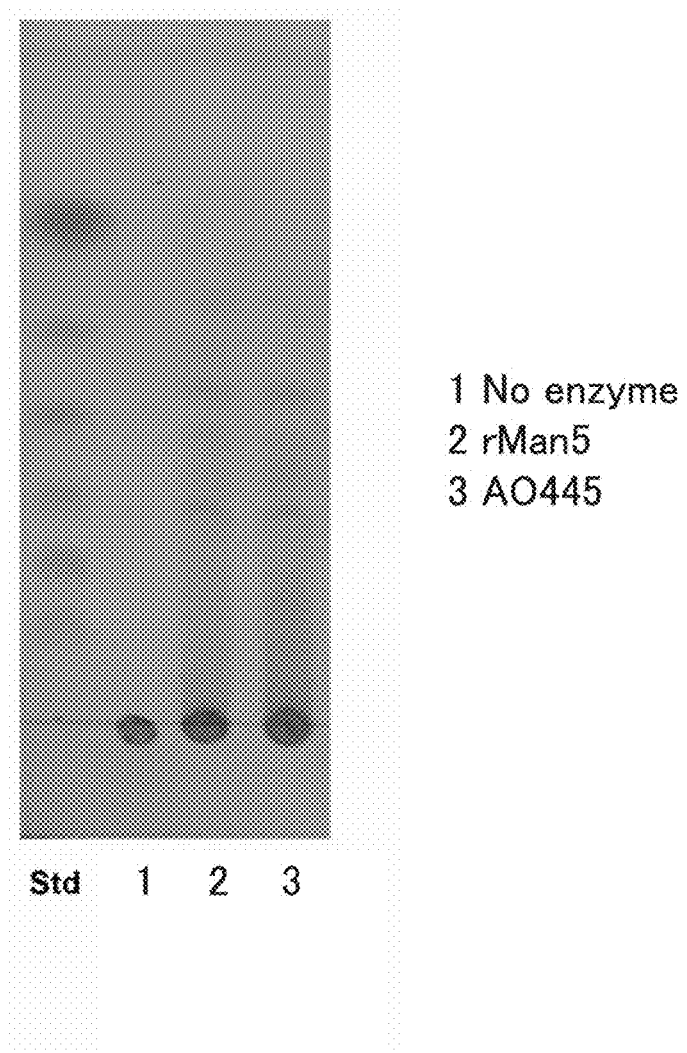
FIG. 13 shows detection of decomposed products from glucomannan mixed with rAO445 or rMan5.

As shown in FIG. 13, the glucomannan decomposed product from rAO445 exhibited similar detection pattern as the decomposed products from rMan5 which is an existing mannanase. The results revealed that AO445 also has endo-1,4-β-mannanase activity.

Figure 14:
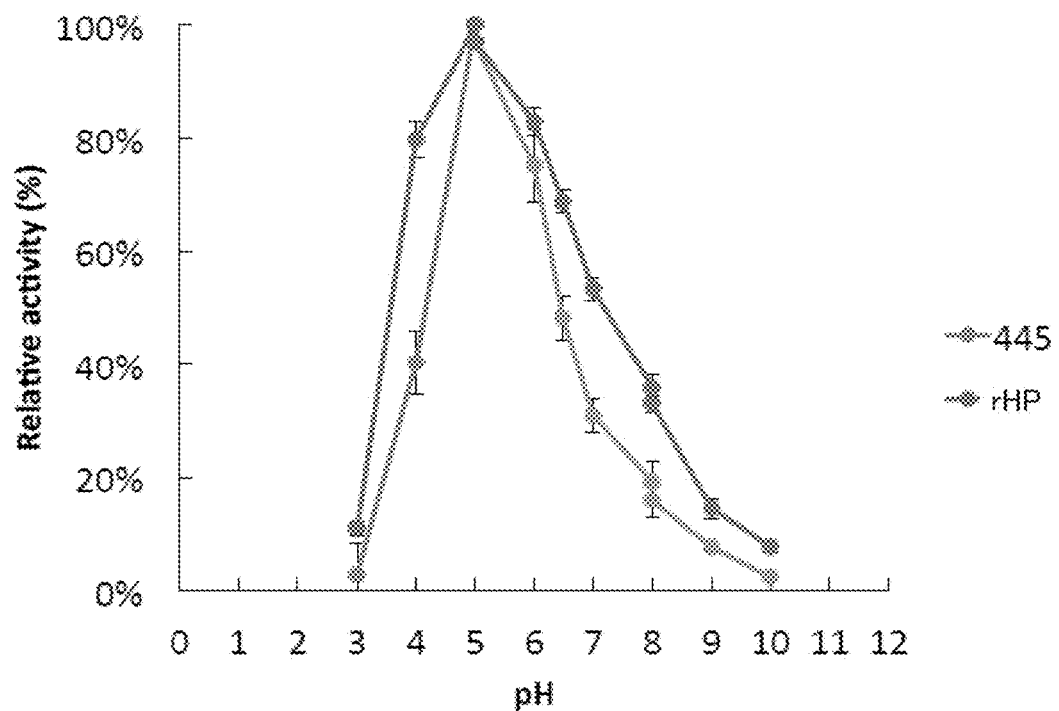
FIG. 14 shows a measurement result on the optimal pH of rAO445.

The present protein was examined for the optimal pH according to Sixth Embodiment. As a result, the optimal pH was 5 as shown in FIG. 14. The present protein, as mannanase on glucomannan, had Km of 1.8±0.2 mg/ml, Kcat of 590/sec and Kcat/Km of 330 ml/mg·sec. The protein had, on galactomannan, Km of 5.1±0.4 mg/ml, Kcat of 290/sec and Kcat/Km of 57 ml/mg·sec.

The optimal temperature was measured according to Sixth Embodiment. As a result, the optimal temperature was about 30° C. and had such heat resistance that the proportion (%) of activity at 80° C. of 70% or more relative to the enzyme activity at 20° C.

Eighth Embodiment

Amino acid sequences (SEQ ID NOs: 4, 6 and 10) of two proteins (6833 and 6951) derived from A. nidulans and a protein (134) derived from Streptomyces. sp were obtained which had high identity with the amino acid sequence of SEQ ID NO: 2 of mannanase derived from *A. nidulans* identified in First Embodiment.

Wild-type *A. nidulans* was cultured in a glucomannan medium in the same manner as in First Embodiment to extract RNA. cDNA was obtained by reverse transcription. Thereafter, the genes encoding the extracted proteins (6833 and 6951) derived from *A. nidulans* were amplified with primers designed based on base sequences (SEQ NOs: 3 and 5) of DNAs respectively encoding the amino acid sequences of the proteins and plasmids for expression were prepared. *E. coli* was transformed with the plasmids and desired proteins were produced and purified.

For the protein corresponding to the fifth mannanase, a base sequence (SEQ ID NO: 9) of DNA encoding the amino acid sequence of WP_030268297.1 registered at NCBI was synthesized. The gene encoding the desired protein was amplified with primers designed based on the base sequence (SEQ ID NO: 9) of DNA and ligated to pET28a to prepare a plasmid for expression. *E. coli* was transformed with the plasmid to produce the desired protein which was then purified.

The substrate specificity of the proteins was examined according to Second Embodiment. As a result, all proteins hydrolyzed galactomannan and glucomannan but did not hydrolyze chitin, xylan and cellulose which are non-mannan carbon sources, similar to rMan5. In addition, all proteins hydrolyzed galactomannan and glucomannan, but did not hydrolyze xylan, chitin, MCC and CMC which are non-mannan carbon sources. The results revealed that the proteins specifically hydrolyze mannan.

In addition, according to Third Embodiment, endo-1,4-β-mannanase activity was examined. As a result, it was revealed that all proteins have endo-1,4-β-mannanase activity.

In addition, according to Fourth Embodiment, the substrate specificity towards mannooligosaccharides was examined. As a result, it was found that the proteins consisting of amino acid sequences of SEQ ID NOs: 4 and 10 could hydrolyze substrates which were mannooligosaccharides of pentasaccharide or above and the protein consisting of the amino acid sequence of SEQ ID NO: 6 could decompose substrates which were mannooligosaccharides of hexasaccharide or above.

Figure 15:
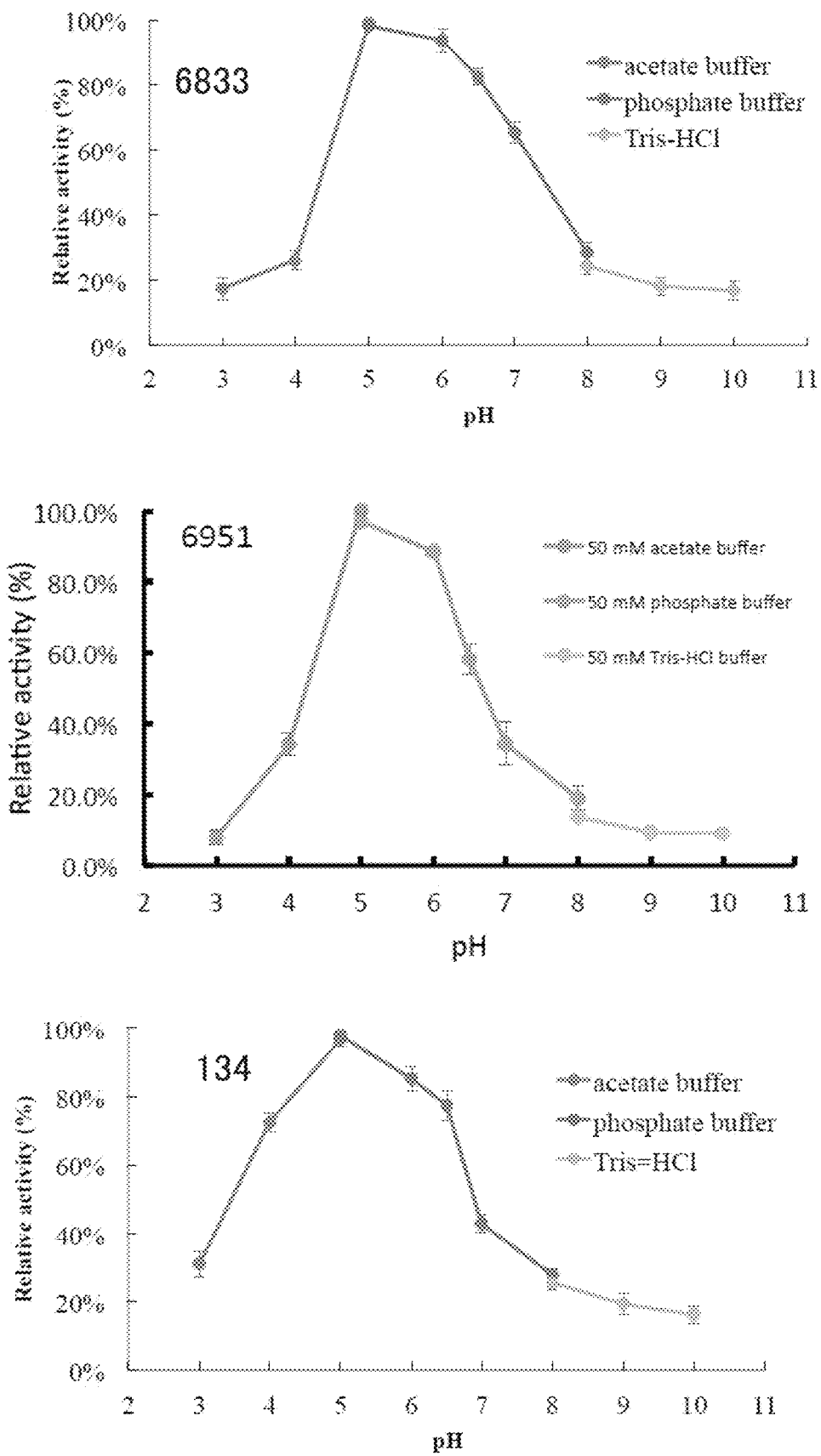
FIG. 15 shows a measurement result on the optimal pH of homologues and orthologues of rHP.

The proteins were examined for the optimal pH, heat resistance and the like according to Sixth Embodiment. The results are shown in FIG. 15. As shown in FIG. 15, all proteins had an optimal pH around pH 5.

Ninth Embodiment

The amino acid sequences of SEQ ID NOs: 2, 4 and 6 which are mannanases derived from *A. nidulans*, the amino acid sequence of SEQ ID NO: 8 which is a mannanase derived from *A. oryzae* and the mannanase of SEQ ID NO: 10 derived from *Streptomyces*. sp were aligned on ClustalW version 2.1. The results are shown in FIG. 16.

As shown in FIG. 16, it was revealed that the proteins have four characteristic motifs. It was also found that in addition to the motifs, the proteins contain 46 common amino acids.

Tenth Embodiment

In the mannanase of SEQ ID NO: 2 derived from *A. nidulans*, alanine was introduced by site specific mutagenesis at candidate sites which may affect the active site found on the basis of, for example, the alignment with homologues and orthologues for which mannanase activity was confirmed. In the present Embodiment, E61A, E63A, D73A, D78A, E106A, W166A and N116A were obtained in the amino acid sequence of SEQ ID NO: 2. In the site specific mutagenesis, primers according to the purpose were obtained by inverse PCR, plasmids for transformation were prepared which contained DNAs encoding proteins having desired mutations and proteins were obtained according to First Embodiment. For the proteins, enzymatic parameters on glucomannan were calculated according to Sixth Embodiment. The results are shown in FIG. 17.

As shown in FIG. 17, E61A and E63A had eliminated mannanase activity. Therefore, it was revealed that positions 61 and 63 of the amino acid sequence of SEQ ID NO: 2 were active sites. In addition, other mutants also exhibited excellent features such as low Km, high kcat and the like. For example, it was revealed that W166A (SEQ ID NO: 19) is a suitable mutant.

SEQUENCE LISTING FREE TEXT

SEQ ID NOs: 13 to 18: Primers
SEQ ID NO: 19: Mutant protein

CITATION LIST

Patent Literature 1: Japanese Translation of PCT Application No. 2013-516960

The invention claimed is:

1. An expression vector comprising a polynucleotide encoding a mannanase selected from the group consisting of (a)-(h):
   (a) a polypeptide having the amino acid sequence of SEQ ID NO: 8;
   (b) a polypeptide having an amino acid sequence which has 90% or more identity with the amino acid sequence of SEQ ID NO: 8;
   (c) a polypeptide having an amino acid sequence derived from the amino acid sequence of SEQ ID NO: 8 by at least one of substitution, deletion and insertion of one or more and 20 or less of amino acids;
   (d) a polypeptide encoded by a base sequence which has 90% or more identity with a base sequence of SEQ ID NO: 7;
   (e) a polypeptide having the amino acid sequence of SEQ ID NO: 4;
   (f) a polypeptide having an amino acid sequence which has 90% or more identity with the amino acid sequence of SEQ ID NO: 4;
   (g) a polypeptide having an amino acid sequence derived from the amino acid sequence of SEQ ID NO: 4 by at least one of substitution, deletion and insertion of one or more and 20 or less of amino acids; and
   (h) a polypeptide encoded by a base sequence which has 90% or more identity with a base sequence of SEQ ID NO: 3.

2. A transformed cell containing the expression vector according to claim 1.

3. The transformed cell according to claim 2, which is *Escherichia coli*.

4. A method for producing mannanase, the method comprising:
   culturing the transformed cell according to claim 2; and
   recovering the mannanase selected from the group consisting of (a) to (h) from the culture.

5. The method according to claim 4, wherein the transformed is *Escherichia coli*.

6. The expression vector according to claim 1, wherein the mannanase is selected from the group consisting of (a)-(d).

7. The transformed cell according to claim 2, wherein the vector comprises the polynucleotide encoding the mannanase selected from the group consisting of (a)-(d).

8. The transformed cell according to claim 3, wherein the vector comprises the polynucleotide encoding the mannanase selected from the group consisting of (a)-(d).

9. The method according to claim 4, wherein the culturing cultures the transformed cell according to claim 7 and the recovering recovers the mannanase selected from the group consisting of (a)-(d).

10. The method according to claim 5, wherein the culturing cultures the transformed cell according to claim 8 and the recovering recovers the mannanase selected from the group consisting of (a)-(d).

* * * * *

SEQUENCE LISTING

```
<160> NUMBER OF SEQ ID NOS: 19

<210> SEQ ID NO 1
<211> LENGTH: 576
<212> TYPE: DNA
<213> ORGANISM: Aspergillus nidulans

<400> SEQUENCE: 1
atgaaaggcc tccaaatatt tgtctcgtct gtcctcacct tgggagctct ggcagccccc      60
acgacggaca tgaccaagag ggcagaccgc ggttcctaca ctgtgtccgg actcgggcag     120
cgcaagcagg ctattttgaa tgcgggtgga aacacccttg atcttgcaat tgccatgctt     180
gagacagagg gaatgacaac cgactacacc tacggtgatg ggaagaccta tgatgccgcc     240
aatttcggtc ttttcaagca gaactggggc atgctccgtg tctgtgccac taggtatggg     300
```

```
ttggccggtc agtctgaggc tgactggaat aatggcgcta tactgaattc gaatgtctat    360
gccgatgtcg cgtcccgctg ggactgccag ggatactacg gcgtcgacct gtggtttgca    420
gggcaccgca atggtgcaag cggattgagt aatccgaata cggatgatat taacaactat    480
aagagtgctg tctactggat ccagcagcag atcgacagta actccgtcta caagaccgat    540
gacacgcgct tttgggttga tgtccaggct atctaa                              576
```

```
<210> SEQ ID NO 2
<211> LENGTH: 191
<212> TYPE: PRT
<213> ORGANISM: Aspergillus nidulans

<400> SEQUENCE: 2
```

```
Met Lys Gly Leu Gln Ile Phe Val Ser Ser Val Leu Thr Leu Gly Ala
1               5                   10                  15

Leu Ala Ala Pro Thr Thr Asp Met Thr Lys Arg Ala Asp Arg Gly Ser
            20                  25                  30

Tyr Thr Val Ser Gly Leu Gly Gln Arg Lys Gln Ala Ile Leu Asn Ala
        35                  40                  45

Gly Gly Asn Thr Leu Asp Leu Ala Ile Ala Met Leu Glu Thr Glu Gly
    50                  55                  60

Met Thr Thr Asp Tyr Thr Tyr Gly Asp Gly Lys Thr Tyr Asp Ala Ala
65                  70                  75                  80

Asn Phe Gly Leu Phe Lys Gln Asn Trp Gly Met Leu Arg Val Cys Ala
                85                  90                  95

Thr Arg Tyr Gly Leu Ala Gly Gln Ser Glu Ala Asp Trp Asn Asn Gly
            100                 105                 110

Ala Ile Leu Asn Ser Asn Val Tyr Ala Asp Val Ala Ser Arg Trp Asp
        115                 120                 125

Cys Gln Gly Tyr Tyr Gly Val Asp Leu Trp Phe Ala Gly His Arg Asn
    130                 135                 140

Gly Ala Ser Gly Leu Ser Asn Pro Asn Thr Asp Asp Ile Asn Asn Tyr
145                 150                 155                 160

Lys Ser Ala Val Tyr Trp Ile Gln Gln Gln Ile Asp Ser Asn Ser Val
                165                 170                 175

Tyr Lys Thr Asp Asp Thr Arg Phe Trp Val Asp Val Gln Ala Ile
            180                 185                 190
```

```
<210> SEQ ID NO 3
<211> LENGTH: 576
<212> TYPE: DNA
<213> ORGANISM: Aspergillus nidulans

<400> SEQUENCE: 3
atgaaaggcc tccagatcct cgtctcatcc atcctcgcct gggggctct ggcagatccc     60 tccgcacaga tggacaagag agctgaccgc ggttcctaca ccgtctccgg acttggccag    120
cgcaagcagg ctatcctgga cgcgggtggg aacactcttg atctcgccat cgccatgctt    180
gagactgagg gaatgaccac cgactacgtc tacggtgatg cgaagaccag ggatgctgcc    240
aacttcggcc ttttcaagca gaactgggc ttgctgcgcg tctgcgctga tcggctggc     300 tttgtcggcc agtccgagga tgagtggaat aatggtgcta aactaaattc ggacgtgtat    360
gccgatgtcg cctcccgctg ggattgccag gaacactatg gcgagcagaa gtggttcgct    420
ggccaccgaa acggtgaaag cggactcaac aatcctaaca cccaggatat caacaactac    480
```
aagaatgccg tctactggat caaggagcaa atcgatagca accctgctca caagtctgat    540
gacacccgct tctgggtcga tgttgtggct atctaa    576

<210> SEQ ID NO 4
<211> LENGTH: 191
<212> TYPE: PRT
<213> ORGANISM: Aspergillus nidulans

<400> SEQUENCE: 4

Met Lys Gly Leu Gln Ile Leu Val Ser Ser Ile Leu Ala Leu Gly Ala
1               5                   10                  15

Leu Ala Asp Pro Ser Ala Gln Met Asp Lys Arg Ala Asp Arg Gly Ser
            20                  25                  30

Tyr Thr Val Ser Gly Leu Gly Gln Arg Lys Gln Ala Ile Leu Asp Ala
        35                  40                  45

Gly Gly Asn Thr Leu Asp Leu Ala Ile Ala Met Leu Glu Thr Glu Gly
    50                  55                  60

Met Thr Thr Asp Tyr Val Tyr Gly Asp Ala Lys Thr Arg Asp Ala Ala
65                  70                  75                  80

Asn Phe Gly Leu Phe Lys Gln Asn Trp Gly Leu Leu Arg Val Cys Ala
                85                  90                  95

Asp Arg Ala Gly Phe Val Gly Gln Ser Glu Asp Glu Trp Asn Asn Gly
            100                 105                 110

Ala Lys Leu Asn Ser Asp Val Tyr Ala Asp Val Ala Ser Arg Trp Asp
        115                 120                 125

Cys Gln Glu His Tyr Gly Glu Gln Lys Trp Phe Ala Gly His Arg Asn
    130                 135                 140

Gly Glu Ser Gly Leu Asn Asn Pro Asn Thr Gln Asp Ile Asn Asn Tyr
145                 150                 155                 160

Lys Asn Ala Val Tyr Trp Ile Lys Glu Gln Ile Asp Ser Asn Pro Ala
                165                 170                 175

His Lys Ser Asp Asp Thr Arg Phe Trp Val Asp Val Val Ala Ile
            180                 185                 190

<210> SEQ ID NO 5
<211> LENGTH: 582
<212> TYPE: DNA
<213> ORGANISM: Aspergillus nidulans

<400> SEQUENCE: 5
atgcaacttc tgtctatcct cagcgccttg tctcttactc ctggcgtgct ctcttcttcg    60
tctacagtct ataaggact gtagcccga gatggtagcc ggggaaatga tactatcacg    120
ggcctgggag ctcgcaagca ggcggtgctg acgctggtg gcaatactcg cgatctagca    180
attgcgatgc tggagaccaa tactatgacg acggattata cctacggaga cggcaagacc    240
ggcgattcca caaacttcgg tatcttcaaa caaaattggt acatgctgcg gcattccgcg    300
tccgattttc tgggacagac cgtggatcag gttgataacg cgccattct caactctaac    360 ttgggcaaag acgtcaaagc tcgccatgaa ggcgaagaga aatatggcta tgaaacctgg    420
ttcgccggcc accgcaatgg agagagtggg gtgcagaacc ctggcacaga cgacatcaag    480
gcatatatcg atgctgtggc gtggatccag gagcagattg agagcgacaa gaagtatcag    540
tctgacgaca ctcggttctg ggtagacgtt cacgcgattt aa    582

<210> SEQ ID NO 6
<211> LENGTH: 193

<212> TYPE: PRT
<213> ORGANISM: Aspergillus nidulans

<400> SEQUENCE: 6

Met Gln Leu Leu Ser Ile Leu Ser Ala Leu Ser Leu Thr Pro Gly Val
1               5                   10                  15

Leu Ser Ser Ser Thr Val Tyr Lys Gly Leu Val Ala Arg Asp Gly
            20                  25                  30

Ser Arg Gly Asn Asp Thr Ile Thr Gly Leu Gly Ala Arg Lys Gln Ala
        35                  40                  45

Val Leu Asp Ala Gly Gly Asn Thr Arg Asp Leu Ala Ile Ala Met Leu
    50                  55                  60

Glu Thr Asn Thr Met Thr Thr Asp Tyr Thr Tyr Gly Asp Gly Lys Thr
65                  70                  75                  80

Gly Asp Ser Thr Asn Phe Gly Ile Phe Lys Gln Asn Trp Tyr Met Leu
                85                  90                  95

Arg His Ser Ala Ser Asp Phe Leu Gly Gln Thr Val Asp Gln Val Asp
            100                 105                 110

Asn Gly Ala Ile Leu Asn Ser Asn Leu Gly Lys Asp Val Lys Ala Arg
        115                 120                 125

His Glu Gly Glu Glu Lys Tyr Gly Tyr Glu Thr Trp Phe Ala Gly His
    130                 135                 140

Arg Asn Gly Glu Ser Gly Val Gln Asn Pro Gly Thr Asp Asp Ile Lys
145                 150                 155                 160

Ala Tyr Ile Asp Ala Val Ala Trp Ile Gln Glu Gln Ile Glu Ser Asp
                165                 170                 175

Lys Lys Tyr Gln Ser Asp Asp Thr Arg Phe Trp Val Asp Val His Ala
            180                 185                 190

Ile

<210> SEQ ID NO 7
<211> LENGTH: 597
<212> TYPE: DNA
<213> ORGANISM: Aspergillus oryzae

<400> SEQUENCE: 7
atgaagttct tcattccctg cattgccgct atcttcgcca ctggagtgct ggccgctcca      60
actcccgatg cttccctcaa tgtccctctc gacaagaggg atgatcgcgg gcaatacacc     120
gtctccggcc tcggatcccg caagaaggcc atcatcgacg cgggcggcaa ctcccttgat     180
ctcgccattg ctatgctcga aatcgagact atgaacaccg cccactatcc ctacggtgac     240
ggcaagacct acgacgccgc caacttcggt ctgttcaagc agaactgggg cttgctccgt     300
gagtgcgccc accgctacgg cttcaagggg aagtcggaag cccaatggaa cgatggagct     360
gtcatgaact cggatgtcta cgccgacgtt gcgtctcgtt gggattgcca gaactattac     420
ggttacgata gtggttcgc tggacaccgc aacggcgctt ctggtcttgc taatccctac     480
actgaggata tcaataccta caagtctgcc gtccattgga tccagcagca gattgacagc     540
aacgagaagt acaagtacga tgacactcgc ttttgggtca atgttcgtgc catctaa      597

<210> SEQ ID NO 8
<211> LENGTH: 198
<212> TYPE: PRT
<213> ORGANISM: Aspergillus oryzae

<400> SEQUENCE: 8

Met Lys Phe Phe Ile Pro Cys Ile Ala Ala Ile Phe Ala Thr Gly Val
1               5                   10                  15

Leu Ala Ala Pro Thr Pro Asp Ala Ser Leu Asn Val Pro Leu Asp Lys
                20                  25                  30

Arg Asp Asp Arg Gly Gln Tyr Thr Val Ser Gly Leu Gly Ser Arg Lys
            35                  40                  45

Lys Ala Ile Ile Asp Ala Gly Gly Asn Ser Leu Asp Leu Ala Ile Ala
        50                  55                  60

Met Leu Glu Ile Glu Thr Met Asn Thr Ala His Tyr Pro Tyr Gly Asp
65                  70                  75                  80

Gly Lys Thr Tyr Asp Ala Ala Asn Phe Gly Leu Phe Lys Gln Asn Trp
                85                  90                  95

Gly Leu Leu Arg Glu Cys Ala His Arg Tyr Gly Phe Lys Gly Lys Ser
            100                 105                 110

Glu Ala Gln Trp Asn Asp Gly Ala Val Met Asn Ser Asp Val Tyr Ala
        115                 120                 125

Asp Val Ala Ser Arg Trp Asp Cys Gln Asn Tyr Tyr Gly Tyr Asp Lys
130                 135                 140

Trp Phe Ala Gly His Arg Asn Gly Ala Ser Gly Leu Ala Asn Pro Tyr
145                 150                 155                 160

Thr Glu Asp Ile Asn Thr Tyr Lys Ser Ala Val His Trp Ile Gln Gln
                165                 170                 175

Gln Ile Asp Ser Asn Glu Lys Tyr Lys Tyr Asp Asp Thr Arg Phe Trp
            180                 185                 190

Val Asn Val Arg Ala Ile
        195

<210> SEQ ID NO 9
<211> LENGTH: 726
<212> TYPE: DNA
<213> ORGANISM: Streptomyces. sp

<400> SEQUENCE: 9

| | |
|---|---|
| atgcgtcgca ccgcttcact gctgggcagc gcggtgggta ccctggcggc cctgacgctg | 60 |
| gccctggcac cgaccgcagc tgcggaaacc gccccgaacg gctatccgta ctgcgctaat | 120 |
| ggtagtgcgt ccgatccgga tggtgatggt tgggctggg aaaacaatcg tagctgtgtg | 180 |
| gttcgcaccg gttcaggctc gggtagcggc tctggtagct ctgcatgccc gagcggtgca | 240 |
| acctgtggtt cttatacggt tggcggtctg ggctctcgta acagcaagt ccgcaatgcc | 300 |
| ggcggtagtt ccctggacct ggctgttgcg atgctggaaa ccgaacgtat ggatacggca | 360 |
| tatccgtacg gcgacaacaa aagtggtgat gccgcaaatt ttggtatttt caaacagaac | 420 |
| tggctgatgc tgcgttccgc atgtgcacag tttggcggtc aaggcgcggg ccagtatgac | 480 |
| aacggcgctg cgctgaacag cagcctgggt caggatgtta gttgtctgca tcagagtcaa | 540 |
| tcccactacg gcctggacgc ttggttcgcg ggtcatcgta atggcgcaag cggtctgagc | 600 |
| agcccgaaca ccgcggatat tgccgcatat aaagctgcgg tttactggat caaagcccaa | 660 |
| ctggacgccg atagcgcaaa cctgggcaat gatacgcgct tttgggtcca ggtgccggcg | 720 |
| atctaa | 726 |

<210> SEQ ID NO 10
<211> LENGTH: 241
<212> TYPE: PRT
<213> ORGANISM: Streptomyces. sp

<400> SEQUENCE: 10

```
Met Arg Arg Thr Ala Ser Leu Leu Gly Ser Ala Val Gly Thr Leu Ala
1               5                   10                  15

Ala Leu Thr Leu Ala Leu Ala Pro Thr Ala Ala Ala Glu Thr Ala Pro
            20                  25                  30

Asn Gly Tyr Pro Tyr Cys Ala Asn Gly Ser Ala Ser Asp Pro Asp Gly
        35                  40                  45

Asp Gly Trp Gly Trp Glu Asn Asn Arg Ser Cys Val Val Arg Thr Gly
50                  55                  60

Ser Gly Ser Gly Ser Gly Ser Ser Ala Cys Pro Ser Gly Ala
65                  70                  75                  80

Thr Cys Gly Ser Tyr Thr Val Gly Gly Leu Gly Ser Arg Lys Gln Gln
                85                  90                  95

Val Arg Asn Ala Gly Gly Ser Ser Leu Asp Leu Ala Val Ala Met Leu
            100                 105                 110

Glu Thr Glu Arg Met Asp Thr Ala Tyr Pro Tyr Gly Asp Asn Lys Ser
        115                 120                 125

Gly Asp Ala Ala Asn Phe Gly Ile Phe Lys Gln Asn Trp Leu Met Leu
    130                 135                 140

Arg Ser Ala Cys Ala Gln Phe Gly Gly Gln Gly Ala Gly Gln Tyr Asp
145                 150                 155                 160

Asn Gly Ala Ala Leu Asn Ser Ser Leu Gly Gln Asp Val Ser Cys Leu
                165                 170                 175

His Gln Ser Gln Ser His Tyr Gly Leu Asp Ala Trp Phe Ala Gly His
            180                 185                 190

Arg Asn Gly Ala Ser Gly Leu Ser Ser Pro Asn Thr Ala Asp Ile Ala
        195                 200                 205

Ala Tyr Lys Ala Ala Val Tyr Trp Ile Lys Ala Gln Leu Asp Ala Asp
    210                 215                 220

Ser Ala Asn Leu Gly Asn Asp Thr Arg Phe Trp Val Gln Val Pro Ala
225                 230                 235                 240

Ile
```

<210> SEQ ID NO 11
<211> LENGTH: 534
<212> TYPE: DNA
<213> ORGANISM: Aspergillus oryzae

<400> SEQUENCE: 11

```
atgaagttct tcattccctg cattgccgct atcttcgcca ctggagtgct ggccgctcca    60
actcccgatg cttccctcaa tgtccctctc gacaagaggg atgatcgcgg gcaatacacc   120
gtctccggcc tcggatcccg caagaaggcc atcatcgacg cgggcggcaa ctcccttgat   180
ctcgccattg ctatgctcga aatcgagact atgaacaccg ccactatcc ctacggtgac   240 ggcaagacct acgacgccgc caacttcggt ctgttcaagc agaactgggg cttgctccgg   300
aaaagctcgg atgtctacgc cgacgttgcg tctcgttggg attgccagaa ctattacggt   360
tacgataagt ggttcgctgg acaccgcaac ggcgcttctg gtcttgctaa tccctacact   420
gaggatatca ataccacaa gtctgccgtc cattggatcc agcagcagat tgacagcaac   480
gagaagtaca agtacgatga cactcgcttt tgggtcaatg ttcgtgccat ctaa          534
```

<210> SEQ ID NO 12
<211> LENGTH: 177
<212> TYPE: PRT

<213> ORGANISM: Aspergillus oryzae

<400> SEQUENCE: 12

Met Lys Phe Phe Ile Pro Cys Ile Ala Ala Ile Phe Ala Thr Gly Val
1               5                   10                  15

Leu Ala Ala Pro Thr Pro Asp Ala Ser Leu Asn Val Pro Leu Asp Lys
            20                  25                  30

Arg Asp Asp Arg Gly Gln Tyr Thr Val Ser Gly Leu Gly Ser Arg Lys
        35                  40                  45

Lys Ala Ile Ile Asp Ala Gly Gly Asn Ser Leu Asp Leu Ala Ile Ala
    50                  55                  60

Met Leu Glu Ile Glu Thr Met Asn Thr Ala His Tyr Pro Tyr Gly Asp
65                  70                  75                  80

Gly Lys Thr Tyr Asp Ala Ala Asn Phe Gly Leu Phe Lys Gln Asn Trp
                85                  90                  95

Gly Leu Leu Arg Lys Ser Ser Asp Val Tyr Ala Asp Val Ala Ser Arg
            100                 105                 110

Trp Asp Cys Gln Asn Tyr Tyr Gly Tyr Asp Lys Trp Phe Ala Gly His
        115                 120                 125

Arg Asn Gly Ala Ser Gly Leu Ala Asn Pro Tyr Thr Glu Asp Ile Asn
    130                 135                 140

Thr Tyr Lys Ser Ala Val His Trp Ile Gln Gln Ile Asp Ser Asn
145                 150                 155                 160

Glu Lys Tyr Lys Tyr Asp Asp Thr Arg Phe Trp Val Asn Val Arg Ala
                165                 170                 175

Ile

<210> SEQ ID NO 13
<211> LENGTH: 33
<212> TYPE: DNA
<213> ORGANISM: Artificial sequence
<220> FEATURE:
<223> OTHER INFORMATION: primer

<400> SEQUENCE: 13
cccaagcttc ggccccacg acggacatga cca                                33

<210> SEQ ID NO 14
<211> LENGTH: 39
<212> TYPE: DNA
<213> ORGANISM: Aitificial sequence

<400> SEQUENCE: 14
ccgctcgagt tagatagcct ggacatcaac ccaaaagcg                         39

<210> SEQ ID NO 15
<211> LENGTH: 38
<212> TYPE: DNA
<213> ORGANISM: Artificial sequence
<220> FEATURE:
<223> OTHER INFORMATION: primer

<400> SEQUENCE: 15
cggggtaccc gcaagggctt tgtgaccacc aaaggcga                          38

<210> SEQ ID NO 16
<211> LENGTH: 40
<212> TYPE: DNA
<213> ORGANISM: Artificial sequence
<220> FEATURE:

<223> OTHER INFORMATION: primer

<400> SEQUENCE: 16
atagtttagc ggccgcctac cgtctccggt tcaacttgtt                                40

<210> SEQ ID NO 17
<211> LENGTH: 30
<212> TYPE: DNA
<213> ORGANISM: Artificial sequence
<220> FEATURE:
<223> OTHER INFORMATION: primer

<400> SEQUENCE: 17
cggggtaccg ctccaactcc cgatgcttcc                                          30

<210> SEQ ID NO 18
<211> LENGTH: 42
<212> TYPE: DNA
<213> ORGANISM: Artificial sequence
<220> FEATURE:
<223> OTHER INFORMATION: primer

<400> SEQUENCE: 18
atagtttagc ggccgcttag atggcacgaa cattgaccca aa                            42

<210> SEQ ID NO 19
<211> LENGTH: 191
<212> TYPE: PRT
<213> ORGANISM: Artificial Sequence
<220> FEATURE:
<223> OTHER INFORMATION: Mutant protein

<400> SEQUENCE: 19

Met Lys Gly Leu Gln Ile Phe Val Ser Ser Val Leu Thr Leu Gly Ala
1               5                   10                  15

Leu Ala Ala Pro Thr Thr Asp Met Thr Lys Arg Ala Asp Arg Gly Ser
                20                  25                  30

Tyr Thr Val Ser Gly Leu Gly Gln Arg Lys Gln Ala Ile Leu Asn Ala
            35                  40                  45

Gly Gly Asn Thr Leu Asp Leu Ala Ile Ala Met Leu Glu Thr Glu Gly
        50                  55                  60

Met Thr Thr Asp Tyr Thr Tyr Gly Asp Gly Lys Thr Tyr Asp Ala Ala
65                  70                  75                  80

Asn Phe Gly Leu Phe Lys Gln Asn Trp Gly Met Leu Arg Val Cys Ala
                85                  90                  95

Thr Arg Tyr Gly Leu Ala Gly Gln Ser Glu Ala Asp Trp Asn Asn Gly
            100                 105                 110

Ala Ile Leu Asn Ser Asn Val Tyr Ala Asp Val Ala Ser Arg Trp Asp
        115                 120                 125

Cys Gln Gly Tyr Tyr Gly Val Asp Leu Trp Phe Ala Gly His Arg Asn
    130                 135                 140

Gly Ala Ser Gly Leu Ser Asn Pro Asn Thr Asp Asp Ile Asn Asn Tyr
145                 150                 155                 160

Lys Ser Ala Val Tyr Ala Ile Gln Gln Gln Ile Asp Ser Asn Ser Val
                165                 170                 175

Tyr Lys Thr Asp Asp Thr Arg Phe Trp Val Asp Val Gln Ala Ile
            180                 185                 190